(12) United States Patent
Auld et al.

(10) Patent No.: US 10,434,010 B2
(45) Date of Patent: Oct. 8, 2019

(54) INTRAOCULAR GAS INJECTOR

(71) Applicant: Altaviz, LLC, Irvine, CA (US)

(72) Inventors: Jack R. Auld, Laguna Niguel, CA (US); John C. Huculak, Mission Viejo, CA (US); Christopher L. McCollam, Irvine, CA (US)

(73) Assignee: Alcon Pharmaceuticals Ltd., Fribourg (CH)

(*) Notice: Subject to any disclaimer, the term of this patent is extended or adjusted under 35 U.S.C. 154(b) by 274 days.

(21) Appl. No.: 15/640,141

(22) Filed: Jun. 30, 2017

(65) Prior Publication Data
US 2017/0325995 A1   Nov. 16, 2017

Related U.S. Application Data

(63) Continuation of application No. 13/916,536, filed on Jun. 12, 2013, now Pat. No. 9,693,895.
(Continued)

(51) Int. Cl.
*A61F 9/00* (2006.01)
*A61F 9/007* (2006.01)
(Continued)

(52) U.S. Cl.
CPC .......... *A61F 9/007* (2013.01); *A61F 9/00727* (2013.01); *A61M 5/3145* (2013.01);
(Continued)

(58) Field of Classification Search
CPC ... A61F 9/007; A61F 9/00727; A61M 5/3156; A61M 5/31553; A61M 5/31596;
(Continued)

(56) References Cited

U.S. PATENT DOCUMENTS 3,004,686 A   10/1961   McKee
3,341,082 A   9/1967    Meshberg
(Continued)

FOREIGN PATENT DOCUMENTS

JP   2004-049726   2/2004
RU   2369368      10/2009
(Continued)

OTHER PUBLICATIONS

International Search Report and Written Opinion in Application No. PCT/US2013/044183 dated Nov. 4, 2013 in 14 pages.
(Continued)

*Primary Examiner* — Amber R Stiles

(57) ABSTRACT

A gas mixture apparatus includes a measurement control system, an activation system, a pressurized chamber with one or more gases, and a mixing chamber. The apparatus can also include additional pressure regulation control systems. The gas mixture apparatus can be used to introduce and automatically perform the steps to achieve a desired concentration of the one or more gases contained in the pressurized chamber. The gas mixture apparatus can include the pressurized chamber within the apparatus itself such that no external devices are necessary for introducing the one or more gases into the mixing chamber.

20 Claims, 27 Drawing Sheets

Related U.S. Application Data

(60) Provisional application No. 61/799,840, filed on Mar. 15, 2013, provisional application No. 61/658,765, filed on Jun. 12, 2012.

(51) Int. Cl.
  *A61M 5/31* (2006.01)
  *A61M 5/315* (2006.01)

(52) U.S. Cl.
  CPC ...... *A61M 5/3156* (2013.01); *A61M 5/31553* (2013.01); *A61M 5/31596* (2013.01); *A61M 5/3158* (2013.01); *A61M 2005/3128* (2013.01); *A61M 2202/02* (2013.01); *A61M 2210/0612* (2013.01)

(58) Field of Classification Search
  CPC .............. A61M 5/3145; A61M 5/3158; A61M 2210/0612; A61M 2005/3128; A61M 2202/02
  See application file for complete search history.

(56) References Cited

U.S. PATENT DOCUMENTS

| | | |
|---|---|---|
| 3,481,323 A | 12/1969 | Cook et al. |
| 3,537,622 A | 11/1970 | Baker et al. |
| 4,429,421 A | 2/1984 | Levy |
| 4,490,351 A | 12/1984 | Clark |
| 4,498,904 A | 2/1985 | Turner et al. |
| 4,573,998 A | 3/1986 | Mazzocco |
| 4,615,703 A | 10/1986 | Callahan et al. |
| 4,619,256 A | 10/1986 | Horn |
| 4,634,423 A | 1/1987 | Bailey, Jr. |
| 4,670,006 A | 6/1987 | Sinnett et al. |
| 4,699,140 A | 10/1987 | Holmes et al. |
| 4,715,373 A | 12/1987 | Mazzocco et al. |
| 4,717,384 A | 1/1988 | Waldeisen |
| 4,726,367 A | 2/1988 | Shoemaker |
| 4,747,404 A | 5/1988 | Jampel et al. |
| 4,760,865 A | 8/1988 | Rilett |
| 4,763,650 A | 8/1988 | Hauser |
| 4,765,329 A | 8/1988 | Cumming et al. |
| 4,822,360 A | 4/1989 | Deacon |
| 4,844,065 A | 7/1989 | Faulkner |
| 4,844,093 A | 7/1989 | Jampel et al. |
| 4,852,566 A | 8/1989 | Callahan et al. |
| 4,862,885 A | 9/1989 | Cumming |
| 4,880,000 A | 11/1989 | Holmes et al. |
| 4,906,247 A | 3/1990 | Fritch |
| 4,919,130 A | 4/1990 | Stoy et al. |
| 4,934,363 A | 6/1990 | Smith et al. |
| 5,007,913 A | 4/1991 | Dulebohn et al. |
| 5,032,111 A | 7/1991 | Morris et al. |
| 5,037,384 A | 8/1991 | Chang |
| 5,047,009 A | 9/1991 | Morris et al. |
| 5,064,413 A | 11/1991 | McKinnon et al. |
| 5,066,276 A | 11/1991 | Wang |
| 5,066,297 A | 11/1991 | Cumming |
| 5,098,439 A | 3/1992 | Hill et al. |
| 5,123,905 A | 6/1992 | Kelman |
| 5,222,972 A | 1/1993 | Hill et al. |
| 5,190,552 A | 3/1993 | Kelman |
| 5,304,182 A | 4/1994 | Rheinish et al. |
| 5,329,975 A | 7/1994 | Heitel |
| 5,334,163 A | 8/1994 | Sinnett |
| 5,336,175 A | 8/1994 | Mames |
| 5,354,333 A | 10/1994 | Kammann et al. |
| 5,487,725 A | 1/1996 | Peyman |
| 5,496,328 A | 3/1996 | Nakajima et al. |
| 5,547,473 A | 8/1996 | Peyman |
| 5,562,676 A | 10/1996 | Brady et al. |
| 5,582,613 A | 12/1996 | Brady et al. |
| 5,582,614 A | 12/1996 | Feingold |
| 5,616,148 A | 4/1997 | Eagles et al. |
| 5,630,821 A | 5/1997 | Klaas |
| 5,643,275 A | 7/1997 | Blake |
| 5,643,276 A | 7/1997 | Zaleski |
| 5,676,888 A | 10/1997 | Kuckens et al. |
| 5,693,057 A | 12/1997 | Dusek |
| 5,716,364 A | 2/1998 | Makker et al. |
| 5,772,666 A | 6/1998 | Feingold et al. |
| 5,772,667 A | 6/1998 | Blake |
| 5,776,138 A | 7/1998 | Vidal et al. |
| 5,803,925 A | 9/1998 | Yang et al. |
| 5,807,400 A | 9/1998 | Chambers et al. |
| 5,810,833 A | 9/1998 | Brady et al. |
| 5,860,984 A | 1/1999 | Chambers et al. |
| 5,868,751 A | 2/1999 | Feingold |
| 5,873,879 A | 2/1999 | Figueroa et al. |
| 5,876,406 A | 3/1999 | Wolf et al. |
| 5,876,407 A | 3/1999 | Makker et al. |
| 5,876,440 A | 3/1999 | Feingold |
| 5,921,989 A | 6/1999 | Deacon et al. |
| 5,944,725 A | 8/1999 | Cicenas et al. |
| 5,947,975 A | 9/1999 | Kikuchi et al. |
| 5,947,976 A | 9/1999 | Van Noy et al. |
| 5,997,498 A | 12/1999 | De Juan, Jr. |
| 6,024,719 A | 2/2000 | Morris |
| 6,050,957 A | 4/2000 | Desch |
| 6,073,759 A | 7/2000 | Lamborne et al. |
| 6,159,161 A | 12/2000 | Hodosh |
| 6,299,618 B1 | 10/2001 | Sugiura |
| 6,312,433 B1 | 11/2001 | Butts et al. |
| 6,334,862 B1 | 1/2002 | Vidal et al. |
| 6,336,932 B1 | 1/2002 | Figueroa et al. |
| 6,342,058 B1 | 1/2002 | Portney |
| 6,371,960 B2 | 4/2002 | Heyman et al. |
| 6,387,101 B1 | 5/2002 | Butts et al. |
| 6,398,789 B1 | 6/2002 | Capetan |
| 6,428,545 B2 | 8/2002 | Portney |
| 6,468,282 B2 | 10/2002 | Kikuchi et al. |
| 6,491,697 B1 | 12/2002 | Clark et al. |
| 6,494,314 B1 | 12/2002 | Lamborne et al. |
| 6,500,181 B1 | 12/2002 | Portney |
| 6,503,275 B1 | 1/2003 | Cumming |
| 6,506,176 B1 | 1/2003 | Mittelstein et al. |
| 6,506,195 B2 | 1/2003 | Chambers et al. |
| 6,533,769 B2 | 3/2003 | Holmén |
| 6,537,281 B1 | 3/2003 | Portney |
| 6,537,283 B2 | 3/2003 | Van Noy |
| 6,540,754 B2 | 4/2003 | Brady |
| 6,554,839 B2 | 4/2003 | Brady |
| 6,558,395 B2 | 5/2003 | Hjertman et al. |
| 6,582,445 B1 | 6/2003 | Koons |
| 6,585,972 B2 | 7/2003 | Peyman |
| 6,599,271 B1 | 7/2003 | Easley |
| 6,599,280 B1 | 7/2003 | Pynson et al. |
| 6,601,609 B2 | 8/2003 | Taylor |
| 6,607,537 B1 | 8/2003 | Binder |
| 6,629,979 B1 | 10/2003 | Feingold et al. |
| 6,666,871 B2 | 12/2003 | Kikuchi et al. |
| 6,679,891 B2 | 1/2004 | Makker et al. |
| 6,685,740 B2 | 2/2004 | Figueroa et al. |
| 6,712,848 B1 | 3/2004 | Wolf et al. |
| 6,723,104 B2 | 4/2004 | Ott |
| 6,726,666 B2 | 4/2004 | De Juan, Jr. |
| 6,733,507 B2 | 5/2004 | McNicholas et al. |
| 6,858,033 B2 | 2/2005 | Kobayashi |
| 6,866,142 B2 | 3/2005 | Lamborne et al. |
| 6,899,877 B2 | 5/2005 | Peyman |
| 6,921,405 B2 | 7/2005 | Feingold et al. |
| 6,923,815 B2 | 8/2005 | Brady et al. |
| 6,976,989 B1 | 12/2005 | Vincent |
| 6,981,612 B2 | 1/2006 | Siimes et al. |
| 6,986,763 B2 | 1/2006 | Holmén |
| 7,025,782 B2 | 4/2006 | Kobayashi et al. |
| 7,033,366 B2 | 4/2006 | Brady |
| 7,037,312 B2 | 5/2006 | Kikuchi et al. |
| 7,037,328 B2 | 5/2006 | Vincent |
| 7,131,976 B2 | 11/2006 | Kobayashi et al. |
| 7,137,994 B2 | 11/2006 | De Juan, Jr. et al. |
| 7,156,855 B2 | 1/2007 | Oda |
| 7,276,071 B2 | 10/2007 | Lin et al. |

(56) References Cited

U.S. PATENT DOCUMENTS

| | | |
|---|---|---|
| 7,279,006 B2 | 10/2007 | Vincent |
| 7,316,676 B2 | 1/2008 | Peyman et al. |
| 7,328,700 B2 | 2/2008 | Baker et al. |
| 7,335,209 B2 | 2/2008 | Meyer |
| RE40,185 E | 3/2008 | Kikuchi et al. |
| 7,348,038 B2 | 3/2008 | Makker et al. |
| 7,422,604 B2 | 9/2008 | Vaquero et al. |
| 7,429,263 B2 | 9/2008 | Vaquero et al. |
| 7,458,976 B2 | 12/2008 | Peterson et al. |
| 7,476,229 B2 | 1/2009 | Meyer |
| 7,476,230 B2 | 1/2009 | Ohno et al. |
| 7,585,291 B1 | 9/2009 | Campion |
| 7,645,300 B2 | 1/2010 | Tsai |
| 7,687,097 B2 | 3/2010 | Makker et al. |
| 7,704,258 B2 | 4/2010 | Feingold et al. |
| 7,740,636 B2 | 6/2010 | Lee et al. |
| 7,744,580 B2 | 6/2010 | Reboul |
| 7,744,603 B2 | 6/2010 | Zadno-Azizi et al. |
| 7,867,240 B2 | 1/2011 | Peterson et al. |
| 7,883,496 B2 | 2/2011 | Campion |
| 7,892,202 B2 | 2/2011 | Lampropoulos et al. |
| 7,892,283 B2 | 2/2011 | Shepherd |
| 7,901,414 B2 | 3/2011 | Tourrette et al. |
| 7,947,049 B2 | 5/2011 | Vaquero |
| 7,988,701 B2 | 8/2011 | Vaquero et al. |
| 8,021,423 B2 | 9/2011 | Tanaka |
| 8,048,085 B2 | 11/2011 | Peterson et al. |
| 8,062,360 B2 | 11/2011 | Pollock |
| 8,080,017 B2 | 12/2011 | Tanaka |
| 8,114,095 B2 | 2/2012 | Rathert |
| 8,123,804 B2 | 2/2012 | Tanaka |
| 8,142,498 B2 | 3/2012 | Tsai |
| 8,152,817 B2 | 4/2012 | Tanaka |
| 8,216,629 B2 | 7/2012 | Mentak |
| 8,246,631 B2 | 8/2012 | Pynson |
| 8,252,053 B2 | 8/2012 | Pynson |
| 8,308,700 B2 | 11/2012 | Campion |
| 8,308,736 B2 | 11/2012 | Boukhny et al. |
| 8,308,799 B2 | 11/2012 | Chen et al. |
| 8,353,314 B2 | 2/2013 | Radford et al. |
| 8,568,367 B2 | 10/2013 | Griffiths |
| 8,986,242 B2 | 3/2015 | Auld et al. |
| 9,693,895 B2 | 7/2017 | Auld et al. |
| 2001/0007942 A1 | 7/2001 | Kikuchi et al. |
| 2002/0193803 A1 | 12/2002 | Portney |
| 2003/0187455 A1 | 10/2003 | Kobayashi et al. |
| 2003/0209455 A1 | 11/2003 | Pynson et al. |
| 2003/0212406 A1 | 11/2003 | Kobayashi et al. |
| 2003/0212407 A1 | 11/2003 | Kikuchi et al. |
| 2003/0216745 A1 | 11/2003 | Brady et al. |
| 2004/0035491 A1 | 2/2004 | Castellano |
| 2004/0059343 A1 | 3/2004 | Shearer et al. |
| 2004/0127911 A1 | 7/2004 | Figueroa et al. |
| 2004/0215207 A1 | 10/2004 | Cumming |
| 2004/0267359 A1 | 12/2004 | Maker et al. |
| 2005/0033308 A1 | 2/2005 | Callahan et al. |
| 2005/0171555 A1 | 8/2005 | Tran et al. |
| 2005/0222577 A1 | 10/2005 | Vaquero |
| 2005/0267403 A1 | 12/2005 | Landau et al. |
| 2005/0267486 A1 | 12/2005 | Holmen |
| 2005/0283162 A1 | 12/2005 | Stratas |
| 2005/0283163 A1 | 12/2005 | Portney et al. |
| 2005/0283164 A1 | 12/2005 | Wu et al. |
| 2006/0085013 A1 | 4/2006 | Dusek et al. |
| 2006/0111667 A1* | 5/2006 | Matsuura ............ A61M 5/3145 604/93.01 |
| 2006/0142780 A1 | 6/2006 | Pynson et al. |
| 2006/0142781 A1 | 6/2006 | Pynson et al. |
| 2006/0167466 A1 | 7/2006 | Dusek |
| 2006/0184181 A1 | 8/2006 | Cole et al. |
| 2006/0264971 A1 | 11/2006 | Akahoshi |
| 2006/0271063 A1 | 11/2006 | Sunada et al. |
| 2006/0287655 A1 | 12/2006 | Khuray et al. |
| 2006/0293694 A1 | 12/2006 | Futamura |
| 2007/0060925 A1 | 3/2007 | Pynson |
| 2007/0203502 A1 | 8/2007 | Makker et al. |
| 2007/0265574 A1 | 11/2007 | Tennican |
| 2007/0270881 A1 | 11/2007 | Hishinuma et al. |
| 2007/0270945 A1 | 11/2007 | Kobayashi et al. |
| 2008/0027460 A1 | 1/2008 | Kobayashi |
| 2008/0027461 A1 | 1/2008 | Vaquero et al. |
| 2008/0033449 A1 | 2/2008 | Cole et al. |
| 2008/0039862 A1 | 2/2008 | Tran |
| 2008/0058830 A1 | 3/2008 | Cole et al. |
| 2008/0082078 A1 | 4/2008 | Berlin |
| 2008/0086146 A1 | 4/2008 | Ishii et al. |
| 2008/0097379 A1 | 4/2008 | Dacquay et al. |
| 2008/0097459 A1 | 4/2008 | Kammerlander et al. |
| 2008/0097460 A1 | 4/2008 | Boukhny et al. |
| 2008/0097461 A1 | 4/2008 | Boukhny et al. |
| 2008/0103432 A1 | 5/2008 | Sanchez et al. |
| 2008/0103433 A1 | 5/2008 | Nazarifar et al. |
| 2008/0147080 A1 | 6/2008 | Pynson |
| 2008/0147081 A1 | 6/2008 | Pynson |
| 2008/0147082 A1 | 6/2008 | Pynson |
| 2008/0154361 A1 | 6/2008 | Pynson et al. |
| 2008/0173835 A1 | 7/2008 | Tomassetti |
| 2008/0208110 A1 | 8/2008 | Sanchez |
| 2008/0208176 A1 | 8/2008 | Loh |
| 2008/0255579 A1 | 10/2008 | Wollenhaupt et al. |
| 2008/0269770 A1 | 10/2008 | Pynson et al. |
| 2009/0005788 A1 | 1/2009 | Rathert |
| 2009/0018548 A1 | 1/2009 | Charles |
| 2009/0024136 A1 | 1/2009 | Martin et al. |
| 2009/0030425 A1 | 1/2009 | Smiley et al. |
| 2009/0036898 A1 | 2/2009 | Ichinohe et al. |
| 2009/0036900 A1 | 2/2009 | Moll |
| 2009/0043313 A1 | 2/2009 | Ichinohe et al. |
| 2009/0112222 A1 | 4/2009 | Barrows et al. |
| 2009/0118680 A1 | 5/2009 | Goldbrunner et al. |
| 2009/0198247 A1 | 8/2009 | Ben Nun |
| 2009/0204122 A1 | 8/2009 | Ichinohe et al. |
| 2009/0234366 A1 | 9/2009 | Tsai et al. |
| 2009/0248031 A1 | 10/2009 | Ichinohe et al. |
| 2009/0254023 A1 | 10/2009 | Akduman |
| 2009/0270876 A1 | 10/2009 | Hoffmann et al. |
| 2009/0292293 A1 | 11/2009 | Bogaert et al. |
| 2009/0318933 A1 | 12/2009 | Anderson |
| 2010/0010498 A1 | 1/2010 | Biddle et al. |
| 2010/0057095 A1 | 3/2010 | Khuray et al. |
| 2010/0076450 A1 | 3/2010 | Yoshida et al. |
| 2010/0082037 A1 | 4/2010 | Kobayashi et al. |
| 2010/0087776 A1 | 4/2010 | Warren |
| 2010/0087832 A1 | 4/2010 | Seyboth |
| 2010/0106160 A1 | 4/2010 | Tsai |
| 2010/0121340 A1 | 5/2010 | Downer |
| 2010/0125278 A1 | 5/2010 | Wagner |
| 2010/0125279 A1 | 5/2010 | Karakelle et al. |
| 2010/0160926 A1 | 6/2010 | Artsyukhovich et al. |
| 2010/0161049 A1 | 6/2010 | Inoue |
| 2010/0185206 A1 | 7/2010 | Ichinohe et al. |
| 2010/0193050 A1 | 8/2010 | Job |
| 2010/0204704 A1 | 8/2010 | Davies et al. |
| 2010/0204705 A1 | 8/2010 | Brown et al. |
| 2010/0217273 A1 | 8/2010 | Someya et al. |
| 2010/0217274 A1 | 8/2010 | Lee et al. |
| 2010/0228260 A1 | 9/2010 | Callahan et al. |
| 2010/0228261 A1 | 9/2010 | Feingold et al. |
| 2010/0256651 A1 | 10/2010 | Jani et al. |
| 2010/0280521 A1 | 11/2010 | Vaquero et al. |
| 2010/0286704 A1 | 11/2010 | Ichinohe et al. |
| 2010/0305577 A1 | 12/2010 | Muchhala et al. |
| 2010/0312254 A1 | 12/2010 | Downer et al. |
| 2011/0046546 A1 | 2/2011 | Rasor et al. |
| 2011/0046633 A1 | 2/2011 | Pankin et al. |
| 2011/0046634 A1 | 2/2011 | Rathert |
| 2011/0046635 A1 | 2/2011 | Pankin et al. |
| 2011/0082463 A1 | 4/2011 | Inoue |
| 2011/0098717 A1 | 4/2011 | Inoue |
| 2011/0144653 A1 | 6/2011 | Pankin et al. |
| 2011/0152872 A1 | 6/2011 | Seyboth et al. |
| 2011/0152873 A1 | 6/2011 | Shepherd |
| 2011/0172676 A1 | 7/2011 | Chen |
| 2011/0190777 A1 | 8/2011 | Hohl |

(56) References Cited

U.S. PATENT DOCUMENTS

| | | |
|---|---|---|
| 2011/0196232 A1 | 8/2011 | Kim et al. |
| 2011/0213380 A1 | 9/2011 | Han |
| 2011/0224677 A1 | 9/2011 | Niwa et al. |
| 2011/0245840 A1 | 10/2011 | Seyboth et al. |
| 2011/0264101 A1 | 10/2011 | Inoue et al. |
| 2011/0270264 A1 | 11/2011 | Shoji et al. |
| 2011/0282273 A1 | 11/2011 | Evans et al. |
| 2011/0288557 A1 | 11/2011 | Kudo et al. |
| 2011/0295264 A1 | 12/2011 | Cole et al. |
| 2011/0313425 A1 | 12/2011 | Han |
| 2012/0016374 A1 | 1/2012 | Han |
| 2012/0016375 A1 | 1/2012 | Peterson et al. |
| 2012/0022547 A1 | 1/2012 | Hildebrand et al. |
| 2012/0022548 A1 | 1/2012 | Zacharias |
| 2012/0071888 A1 | 3/2012 | Putallaz et al. |
| 2012/0130390 A1 | 5/2012 | Davies et al. |
| 2012/0158007 A1 | 6/2012 | Brown et al. |
| 2012/0165824 A1 | 6/2012 | Tsai |
| 2012/0245530 A1 | 9/2012 | Oden |
| 2012/0245591 A1 | 9/2012 | Matthews |
| 2012/0253332 A1 | 10/2012 | Moll |
| 2012/0253356 A1 | 10/2012 | Niwa et al. |
| 2012/0289969 A1 | 11/2012 | Seyboth et al. |
| 2012/0289970 A1 | 11/2012 | Pynson |
| 2012/0323173 A1 | 12/2012 | Thorne et al. |
| 2013/0012956 A1 | 1/2013 | Mirlay |
| 2013/0041382 A1 | 2/2013 | Ben Nun |
| 2013/0090603 A1 | 4/2013 | Hoyle |

FOREIGN PATENT DOCUMENTS

| | | |
|---|---|---|
| WO | WO 03/033363 | 4/2003 |
| WO | WO 05/102421 | 11/2005 |
| WO | WO 07/098622 | 9/2007 |
| WO | WO 07/112130 | 10/2007 |
| WO | WO 08/057672 | 5/2008 |
| WO | WO 10/028873 | 3/2010 |

OTHER PUBLICATIONS

International Search Report and Written Opinion in Application No. PCT/US2013/045515 dated Sep. 5, 2013 in 21 pages.

* cited by examiner

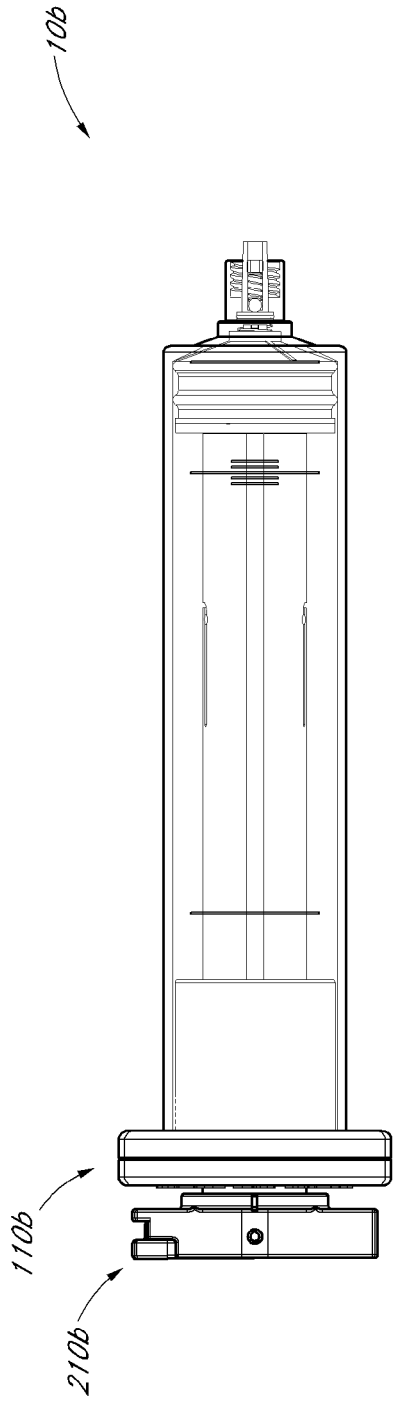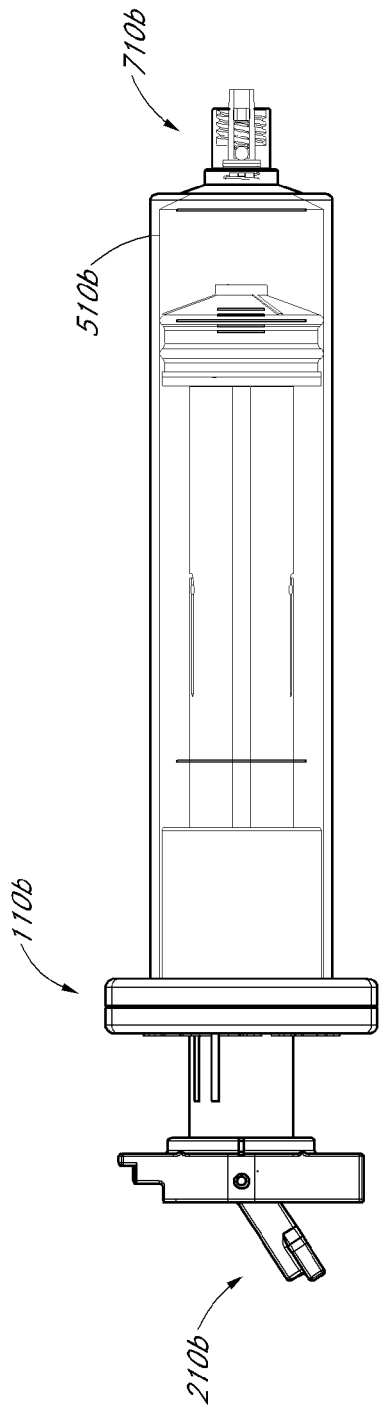
FIG. 2A
FIG. 2B

INTRAOCULAR GAS INJECTOR

RELATED APPLICATIONS

The present application is a continuation application of U.S. patent application Ser. No. 13/916,536 filed Jun. 12, 2013, entitled INTRAOCULAR GAS INJECTOR, which claims priority to U.S. Provisional Application No. 61/658,765 filed Jun. 12, 2012, entitled INTRAOCULAR GAS INJECTOR and U.S. Provisional Application No. 61/799,840 filed Mar. 15, 2013, entitled INTRAOCULAR GAS INJECTOR, the entire contents of each of which are hereby expressly incorporated by reference.

TECHNICAL FIELD

The inventions disclosed herein generally relate to devices and methods for injecting gases into an eye of an animal.

BACKGROUND OF THE INVENTIONS

Surgical procedures can require gases or other fluids to be injected into a target area for treatment of certain injuries, disorders and diseases. In the treatment of eye conditions such as macular holes, retinal tears and detachments, part of the surgical procedure can include the injection of gases or other fluids into the eye.

For example, retinal detachment is an eye disorder involving the separation of the retina from the Retinal Pigment Epithelium (RPE), the tissue that holds the retina in place. Retinal detachment can occur due to a retinal tear, traction on the retina, or inflammation which allows fluid to build up in the subretinal space thereby causing the retina to begin to separate from supporting RPE tissue. This disorder can also occur due to Posterior Vitreous Detachment (PVD), Proliferative Diabetic Retinopathy (PDR), injury, or neovascularization of the fibrous or vascular tissue causing the retina to be detached from the RPE. Such a condition, if not treated immediately, could lead to partial vision loss and potentially even blindness.

Treatment approaches for uncomplicated retinal detachments may include non-surgical techniques such as pneumatic retinopexy, laser photocoagulation, or cryopexy. More complicated retinal detachments require surgical intervention. Due to the risk of infection, which can potentially cause blindness, such surgeries are performed under sterile conditions in order to significantly reduce the potential for infection. Surgical methods include vitrectomy, which is the removal of the vitreous humor; dissection and removal of membranes, in the case of traction retinal detachments; and photocoagulation or cryopexy, in the case of additional retinal tears. Following such a surgical procedure, an intraocular gas tamponade may be used to hold the retina tissue in contact with the RPE which enables the retina to remain attached during the healing process after the surgical procedure.

Since intraocular pressure must be maintained relatively constant during the healing process, the gas chosen is typically one that expands at constant pressure (isobaric process). As such, the intraocular gas tamponade can be a gas bubble of air mixed with an expansile gas such as sulfur hexafluoride ($SF_6$), hexafluroethane ($C_2F_6$), or octafluoropropane ($C_3F_8$). The intraocular gas tamponade dissolves over time depending on the gas and concentrations used. For example, sulfur hexafluoride dissolves within 1-2 weeks when mixed with air at a concentration of approximately 20 percent, hexafluoroethane dissolves in approximately 4-5 weeks when mixed with air at a concentration of approximately 16 percent, and octafluoropropane dissolves in approximately 6-8 weeks when mixed with air at a concentration of approximately 12%. Changing the concentrations of these gases affects the duration.

Current practice involves use of gases contained in separate, multi-dose pressurized containers which are then transferred into a syringe for mixing with air and injection into the patient's eye. Therefore, during a surgical procedure, multiple non-sterile and sterile steps are required in order to fill the syringe with a desired concentration of gas and air. These non-sterile and sterile steps are typically performed by the non-sterile operating room circulating nurse and the sterile scrub technician supporting the surgeon in the sterile field. During a first non-sterile step, the circulating nurse prepares the non-sterile re-usable gas container by setting a pressure regulator connected to the gas container at the proper pressure. During a second step, the scrub tech prepares a sterile syringe by connecting a stopcock, filter, and tubing, in series, onto the syringe. During a third step, the tubing is connected to the gas container. The scrub tech carefully passes the free end of the sterile tubing through the invisible sterile barrier to the awaiting non-sterile circulating nurse. The non-sterile circulating nurse receives the tubing and carefully ensures that he/she does not contaminate the scrub tech nor any other of the sterile surfaces; and connects the tubing to the regulator on the gas container. During a fourth step, the syringe is then filled with gas from the container. The scrub tech and circulating nurse coordinate the opening of the pressurized container valve to release gas through the connected tubing, filter, stopcock, and into the syringe. The pressure of the released gas is sufficient to push the syringe plunger along the length of the syringe barrel and thus fill the syringe with gas. The scrub tech ensures that the gas does not push the plunger out of the open end of the syringe barrel and signals to the circulating nurse to close the gas container valve when the syringe approaches a fully filled condition. During a fifth step, the syringe is then purged of all air and gas in order to ensure that a substantial majority of air which may have been present within the syringe, stopcock, filter, and tubing, prior to filling with gas has been purged. The scrub tech turns the stopcock, to provide a means for the air and gas in the syringe to be released to the atmosphere, presses on the syringe plunger, and empties the syringe of all of its contents. The scrub tech then turns the stopcock in the opposite direction, returning the connection pathway to the tubing and the gas container. Steps four and five are repeated several times to further reduce the amount of air that was initially in the syringe, stopcock, filter, and tubing; flushing the majority of the air from the syringe, stopcock, filter, and tubing and purging the system of air. During a sixth step, the syringe is then refilled with gas from the container. The scrub tech detaches the tubing from the filter and signals the circulating nurse to carefully take the tubing, removing it from the sterile field. During a seventh step, the scrub tech does not expel the full contents of the syringe, stopping the plunger such that only a measured volume of gas remains in the syringe. For example, the gas may be expelled such that only 12 mL remains within the syringe. During an eighth step, the scrub tech replaces the used filter with a new sterile filter and draws filtered room air into the syringe until the total air/gas mixture in the syringe is at a proper volume for the desired gas concentration.

For example, atmospheric air may be drawn into the syringe such that the total volume of air and gas is 60 mL therefore achieving a concentration of 20 percent. Since the pressurized containers are non-sterile, and the syringe and surgical area are sterile, completing the above-mentioned steps must be performed by at least one party in the non-sterile field (typically the circulating nurse), a second party in the sterile field (typically the scrub tech), and requires the coordination and communication between the two parties.

The procedure requires a complex set of steps which may increase the potential for errors occurring. An error in one of these steps can result in an improper concentration of gas being used which may result in having either an elevated pressure or reduced retinal tamponade duration thereby potentially causing ischemia or failure of the reattachment surgery, both of which potentially causing blindness. Additionally, the current practice results in a significant amount of wasted gas which is both expensive and harmful to the environment. Thus handling of such gases, especially in pressurized containers containing more than one dose, may present potential danger to the operator if mishandled. As such, some countries may even prohibit storage of these pressurized containers in the operating room.

While there have been some approaches to improve the current procedure, such as U.S. Pat. No. 6,866,142 to Lamborne et al., single-dose containers capable of being placed in the sterile field, and the Alcon® Constellation® system which allows filling and purging of gas, these approaches have been insufficient to address all the potential issues. As such, there remains a need in the industry for an improved gas mixing apparatus.

SUMMARY OF THE INVENTION

An aspect of at least one of the inventions disclosed herein includes the realization that an intraocular gas injector design can allow a surgeon or a nurse to prepare a gas mixture with a selected concentration level using a simplified procedure. For example, in some known intraocular gas injector devices and procedures, such as conventional syringes, multiple parties can be required to fill the syringe to achieve a desired concentration with one person repeatedly filling and discharging the syringe and another person controlling the flow of a gas contained in an external tank. Additionally, each person must coordinate their actions and perform a multitude of complex steps. This increases the potential for errors in the filling process which could result in an improper concentration being achieved in the syringe prior to injection into a patient. Furthermore, this can increase the time necessary to fill the syringe as the two parties must coordinate their activities and perform multiple steps. The potential for error can be particularly dangerous in certain medical fields, such as ophthalmology, where injection of an improper concentration can result in blindness. Thus, an intraocular gas injector that can be operated by a single person can help reduce the likelihood of error.

Another aspect of at least one of the inventions disclosed herein includes the realization that an intraocular gas injector design can allow for multiple selectable concentration levels thereby allowing one device to be used for different applications and thus potentially further reducing manufacturing costs and waste. For example, some conventional devices can only allow for a preset concentration level to be achieved within the device thereby necessitating the manufacturing and storage of multiple devices having different preset concentration level. This increases both the costs of manufacturing and the cost to a surgeon who needs to purchase multiples of each device to accommodate for different surgical needs. Under such circumstances, some devices can expire thereby requiring the manufacturer or surgeon to dispose of such devices without ever having been used. As such, an intraocular gas injector that allows for multiple concentration levels can serve as a one-size fits all for a surgeon thereby reducing waste.

Another aspect of at least one of the inventions disclosed herein includes the realization that an intraocular gas injector design can allow for automated operation during at least some phases of operation thereby reducing the potential for errors in achieving a proper concentration level. For example, in some known intraocular gas injector devices and procedures, such as conventional syringes, a nurse or other operating room personnel must physically measure the amount of gas contained within a syringe during a first phase of operation. In a situation where a minute change in volume can result in a significant change in concentration, a minor error in this physical measurement can result in an improper concentration being achieved in the syringe after all phases of operation have been completed. Therefore, an intraocular gas injector that automatically measures the volume in the first phase and/or any other phase can reduce the likelihood of an improper concentration being achieved in the injector.

Another aspect of at least one of the inventions disclosed herein includes the realization that an intraocular gas injector design can be made with a canister within the injector, with the canister capable of being filled separately prior to incorporation into the injector, thereby reducing the costs of manufacture. Thus, for example, an intraocular gas injector device can include a separate canister placed within the body of the injector.

Yet another aspect of at least one of the inventions disclosed herein includes the realization that an intraocular gas injector design can incorporate a storage member having an internal valve mechanism thereby reducing the costs of manufacture of the injector. For example, in some designs, the device can use multiple pressure regulation systems, such as check valves, integrated on components of the device to regulate pressure within the device and to control the operation of the device. The integration of pressure regulation systems on components of the device can result in increased manufacturing costs for those components. Thus, the relocation of valves to the storage member can help reduce manufacturing costs of the device if the cost of manufacturing of an internal valve mechanism within the storage member is lower than the cost of manufacturing a valve integrated on other components of the device.

An aspect of at least one of the inventions disclosed herein includes the realization that an intraocular gas injector design can incorporate an interlock mechanism configured to control the movement of an activation switch thereby reducing potential erroneous operation of the injector. For example, in some designs, the device can include an activation switch which can control the operation of the device such as the opening and closing of a pressurized chamber within the device. In some instances, the user can use the activator switch to reopen the pressurized chamber within the device when such opening can cause an improper concentration to be received. An interlock mechanism configured to control the movement of an activation switch can help reduce the likelihood of erroneous operation of the injector.

An aspect of at least one of the inventions disclosed herein includes the realization that an intraocular gas injector design can allow for automated operation during at least some phases of operation when connected to an external pressurized chamber thereby reducing the potential for errors in achieving a proper concentration level. For example, in some known intraocular gas injector devices and procedures, such as conventional syringes, a nurse or other operating room personnel can connect an external gas tank to the syringe and repeatedly fill and discharge gas within the syringe to ensure that the syringe contains mainly gas from the tank. During these refill and discharge cycles, another party may need to open and close a valve on the external gas tank. Thus, for example, an intraocular gas injector can allow the attachment of an external pressurized chamber and automatically reach a configured volume and discharge gas such that the injector contains mainly gas from the external pressurized chamber.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

FIG. 2A is a second embodiment of a gas mixture apparatus shown in an initial phase of operation.

FIG. 2B is a second embodiment of a gas mixture apparatus shown in a first phase of operation.

DETAILED DESCRIPTION OF THE PREFERRED EMBODIMENT

Figure 1:
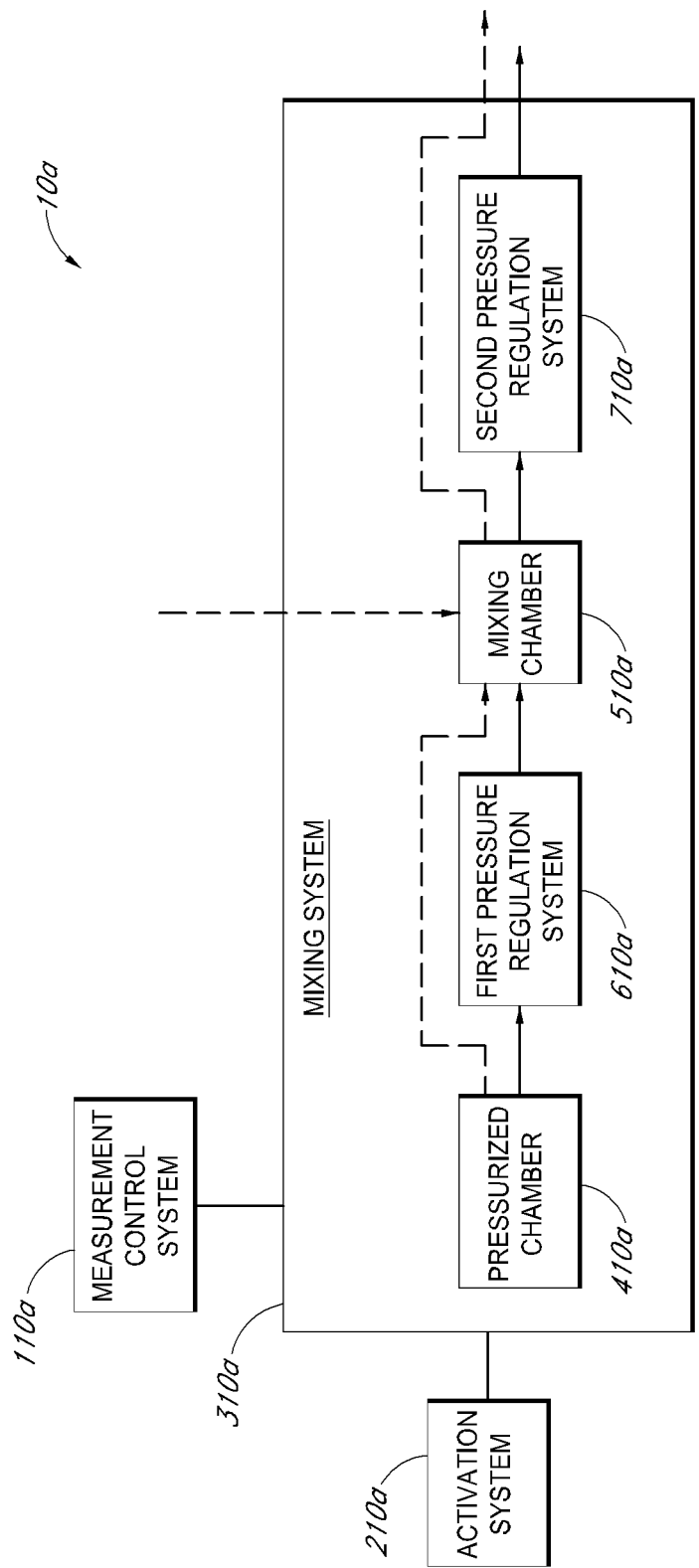
FIG. 1 is a first embodiment of a gas mixture apparatus.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the proceeding technical field, background, brief summary, or the following detailed description.

Certain terminology may be used in the following description for the purpose of reference only, and thus are not intended to be limiting. For example, terms such as "upper", "lower", "above", and "below" refer to directions in the drawings to which reference is made. Terms such as "proximal", "distal", "front", "back", "rear", and "side" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures.

As used herein, the terms "front" and "distal" refer to the parts of the subject apparatus which are located further away from the user (e.g., surgeon) of the apparatus during an injection operation. As used herein, the terms "rear" and "proximal" refer to the parts of the apparatus which are located closer to the user (e.g., surgeon) of the apparatus during an injection operation.

Apparatus for Mixing Two Gases

With reference to FIG. 1, an embodiment of a gas mixture apparatus 10a can comprise a measurement control system 110a, an activation system 210a, and a mixing system 310a configured to create a mixture of two or more gases at a desired concentration ratio. The mixing system 310a can include a pressurized chamber 410a and a mixing chamber 510a.

The mixing system 310a can also include a pressure regulation system to enhance the operation of the mixing system 310a. In some embodiments, the mixing system 310a additionally includes a first pressure regulation system 610a and a second pressure regulation system 710a.

The measurement control system 110a can be in the form of a metering mechanism operatively coupled to any and all devices contained within the mixing system 310a to control certain aspects of the devices contained therein. In some embodiments, the measurement control system 110a can be a variable and user-operable device such that aspects of the device can be modified by the user of the gas mixture apparatus 10a. The activation system 210a can be operatively coupled to the pressurized chamber 410a in order to activate operation of the device and commence the mixing of gases within the mixing system 310a.

The pressurized chamber 410a can contain at least one of the two or more gases to be mixed within the mixing system 310a. In some embodiments, the gas contained within the pressurized chamber 410a can be at a pressure higher than surrounding ambient conditions. Additionally, the pressurized chamber 410a can contain gases at concentrations different from that in the atmosphere. The pressurized chamber 410a can be configured such that it is in fluid communication with the first pressure regulation system 610a. In other embodiments, the pressurized chamber 410a can be in direct fluid communication with the mixing chamber 510a. The pressurized chamber 410a can be configured such that it is internally contained within an injector apparatus. The pressurized chamber 410a can also be configured such that it is external to the injector apparatus. The first pressure regulation system 610a can be configured to maintain a pre-configured pressure differential between the pressurized chamber 410a and the mixing chamber 510a. The mixing chamber 510a can be configured to receive gas from the pressurized chamber 410a either directly or via the first pressure regulation system 610a. In some embodiments, the mixing chamber 510a can additionally be configured to receive a second gas to be mixed from outside the mixing system 310a such as an external gas container or the atmosphere. The mixing chamber 510a can be configured such that it is in fluid communication with the second pressure regulation system 710a at a mixing chamber 510a exit point. In other embodiments, the mixing chamber 510a can be in direct fluid communication with the atmosphere at a mixing chamber exit point. Examples of each of these subsystems are described separately below.

In some embodiments, the measurement control system 110a is configured to control concentrations of the gas within the gas mixture apparatus 10a. In some embodiments, the measurement control system 110a is operatively coupled with the mixing system 310a. Preferably, measurement control system 110a is operatively coupled with either the pressurized chamber 410a or the mixing chamber 510a such that the measurement control system 110a can modify variable aspects of the pressure chamber 410a and/or the mixing chamber 510a. In some embodiments, the measurement control system 110a is capable of controlling characteristics such as, but not limited to, the volume of gas contained within the mixing chamber 510a. Other characteristics, such as pressure, are also contemplated as being controllable by the measurement control system 110a. Preferably, the measurement control system 110a is variable such that a user can be able to select a desired concentration ratio of gas that can be expelled from the gas mixture apparatus 10a. This advantageously allows a user to have only a single gas mixture apparatus 10a for a wide range of desired concentration ratios. As such, the measurement control system 110a can include user-operable switches such as dials which vary the operation of components within the mixing system 310a such as the pressurized chamber 410a, the mixing chamber 510a, the first pressure regulation system 610a, and the second pressure regulation system 710a.

The pressurized chamber 410a is configured to store one or more gases within an interior space of the pressurized chamber 410a for a period of time prior to mixing the two or more gases in the gas mixture apparatus 10a. The conditions within the interior space is configured to be different than those of atmospheric conditions and therefore the interior space should generally reduce the release of such gases out of the interior space or reduce the entry of non-stored gases into the interior space until mixing of the two or more gases is to be performed.

In some embodiments, the one or more gases within the interior space are at a higher pressure than ambient atmospheric conditions. Additionally, the one or more gases can also be gases at concentrations different than those at ambient atmospheric conditions. In some embodiments, the interior space can be divided into separate subsections or portions for holding one or more gases. These separate portions of the interior space can therefore be kept at different pressures and/or different concentrations of gases.

In some embodiments, the gases can additionally be placed in different structural units within the interior space. Such structural units can be used to more effectively reduce the release of stored gases and/or reduce the entry of non-stored gases. In some embodiments, the stored gases of the pressurized chamber 410a are pre-loaded from the time of manufacture. In other embodiments, it is contemplated that the contents of the pressurized chamber 410a can be loaded by a user of the gas mixture apparatus 10a. For example, the stored gases can be contained in a removable cartridge-like device which can advantageously facilitate the replacement of such gases.

In some embodiments, the activation system 210a is configured to activate the operation of the gas mixture apparatus 10a and commence the process of mixing the two or more gases within the mixing system 310a. As such, the activation system 210a is operatively coupled to the mixing system 310a and can be coupled to both the mixing chamber 310a and the pressurized chamber 410a. The activation system can cause the pressurized chamber 410a to activate and release gases contained therein into the mixing chamber 510a. In some preferred embodiments, the activation system 210a can cause the pressure within the pressurized chamber 410a to increase such that the first pressure regulation system 610a is activated thereby allowing fluid flow from the pressurized chamber 410a into the mixing chamber 510a. The activation system 210a can include a device configured to activate a separate portion of the pressurized chamber 410a that contains higher pressure gas than the remainder of the pressurized chamber 410a such that the pressure within a separate section of the pressurized chamber 410a increases. In a preferred embodiment, the activation system 210a can cause a sealed device within the mixing chamber 510a to burst thereby increasing the pressure throughout the pressurized chamber 410a. In such embodiments, the activation system 210a can include a puncturing device capable of bursting the seal. Use of an activation system 210a provides advantages by allowing the gas mixture apparatus 10a to potentially be pre-filled prior to use and safely stored.

The activation system 210a can also be operably coupled to the mixing chamber 510a allowing a user to manually vary certain aspects of the device. In some embodiments, the activation system 210a can be used to modify the volume of the mixing chamber 510a. The activation system 510a can also be used to modify the pressure of the mixing chamber 510a.

In some embodiments, the first pressure regulation system 610a is configured to serve as a separation mechanism between both the pressurized chamber 410a and the mixing chamber 610a. The first pressure regulation system 610a can activate upon reaching a pre-configured pressure differential between both the pressurized chamber 410a and the mixing chamber 510a. In some preferred embodiments, the first pressure regulation system 610a can be comprised of at least one valve assembly. The valve assembly can open when pressure within a portion of the pressurized chamber 410a is higher than the pressure in the mixing chamber 510a. The valve assembly can be a check valve, clack valve, non-return valve, or one-way valve. Such valves can also include ball check valves, diaphragm check valves, swing check valves, stop-check valves, lift-check valves, in-line check valves, and duckbill valves. Other pressure regulation mechanisms can also be used. Additionally, it is contemplated that first pressure regulation system 610a can also be activated by other means other than pressure differentials across the system 610a.

In some embodiments, the mixing chamber 510a is configured to serve as a space within which the two or more gases can be mixed to obtain a desired concentration ratio of the gases. The mixing chamber 510a can be such that the volume can be variable and adjustable based upon use of the activation mechanism. The mixing chamber 510a can receive the gases to mix solely from the pressurized chamber or from gases already existing within the mixing chamber 510a. The mixing chamber 510a can also receive gases from secondary sources. In some embodiments, the mixing chamber 510a can receive air from the atmosphere to mix with the gases received from the pressure chamber 310a and/or gases already existing within the mixing chamber 510a.

In some embodiments, the second pressure regulation system 710a is configured to serve as a separation mechanism between both the mixing chamber 510a and the surrounding atmosphere. The second pressure regulation system 710a can activate upon reaching a pre-configured pressure differential between both the mixing chamber 510a and the surrounding atmosphere. In some preferred embodiments, the second pressure regulation system 710a can be comprised of at least one valve assembly. The valve assembly can open when pressure in the mixing chamber 510a is higher than the pressure in the surrounding atmosphere. The valve assembly can be a check valve, clack valve, non-return valve, or one-way valve. Such valves can also include ball check valves, diaphragm check valves, swing check valves, stop-check valves, lift-check valves, in-line check valves, and duckbill valves. Other pressure regulation mechanisms can also be used. Additionally, it is contemplated that second pressure regulation system 710a can also be activated by other means other than pressure differentials across the system 710a.

Operational Overview

Figure 2C:
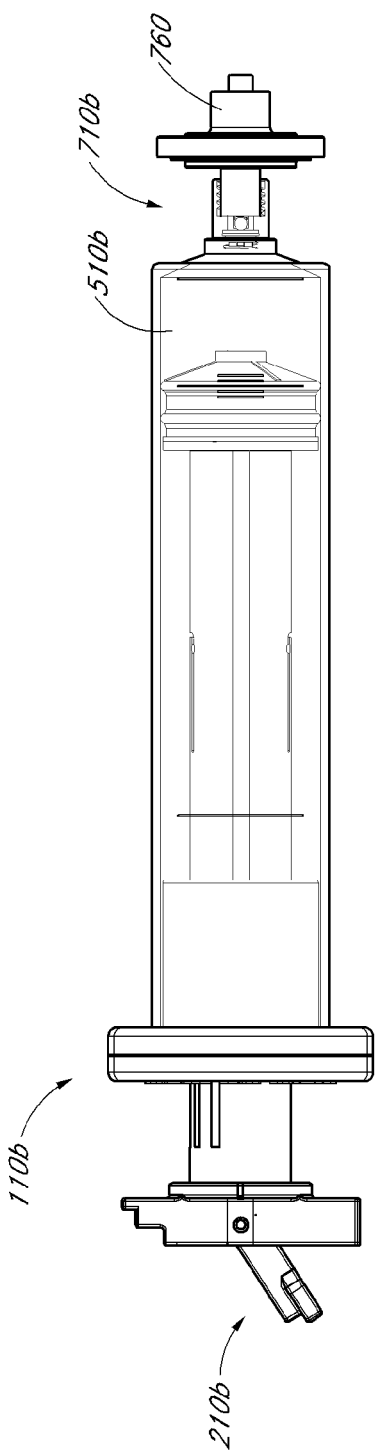
FIG. 2C is a second embodiment of a gas mixture apparatus shown in a second phase of operation.
Figure 2D:
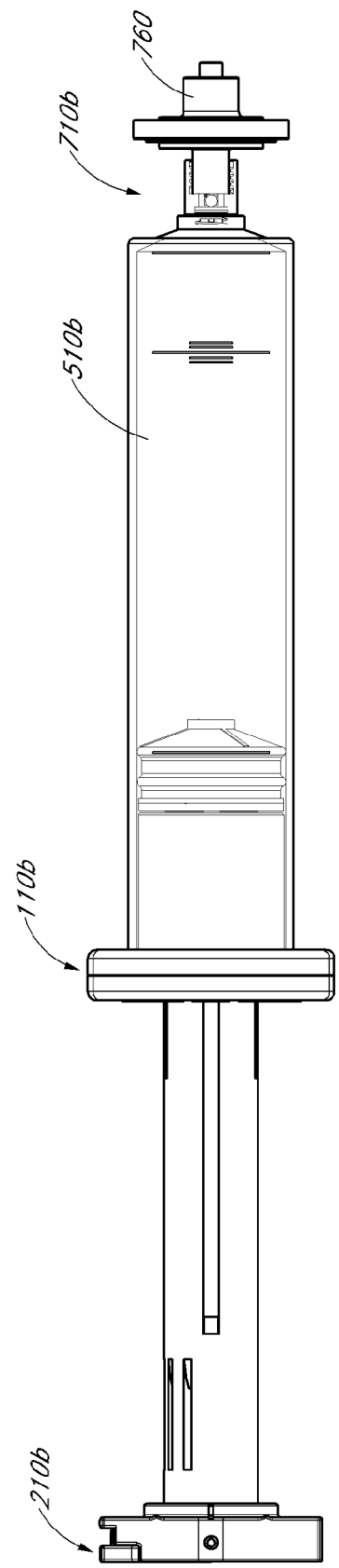
FIG. 2D is a second embodiment of a gas mixture apparatus shown in a third phase of operation.

With reference to FIGS. 2A-2D, the operation of an embodiment of a gas mixture apparatus 10b is illustrated. With reference to FIG. 2A, the apparatus 10b can be in an initial phase with the activation system 210b in a first or "closed" position. At this time, the user of the device can use the measurement control system 110b to select a desired concentration of gas for the injectable volume. Once the selection has been made, the user can then move the activation system 210b into a second or "open" position thereby causing the system to activate and commencing the mixing process.

During this first phase of operation, as shown in FIG. 2B, gas contained within the pressurized chamber can be released and, in embodiments containing a first pressure regulation system, the first pressure regulation system can open in response to a change in pressure within the chamber. As such, fluid can flow from the pressurized chamber into the mixing chamber 510b thereby causing an increase in the volume of the mixing chamber 510b. However, due to components of the measurement control system 110b, the mixing chamber 510b can reach a first volume and cannot expand beyond this first volume. This first volume can be set based on the desired concentration of the injectable volume. During this first phase of operation, excess gas can also be bled from the mixing chamber 510b via the second pressure regulation system 710b. Once the mixing chamber has reached this first volume, the first phase of operation is complete and the second phase of operation begins.

During the second phase of operation, the mixing chamber 510b can remain at the first volume while pressure within the mixing chamber 510b is bled from the system via the second pressure regulation system 710b. By overfilling the mixing chamber 510b with the desired gas, and then bleeding off that gas, this helps to ensure that a significant amount of atmospheric gas within the mixing chamber 510b, which may have been contained in the mixing chamber 510b prior to activation, is substantially purged from the mixing chamber 510b and displaced by the gas originally contained in the pressurized chamber. Once the pressure within the mixing chamber 510b has reached a configured value based on the configuration of the second pressure regulation system 710b, bleeding of the gas within the mixing chamber 510b ceases and the second phase of operation is complete.

During a third phase of operation, as shown in FIG. 2C, an attachment 760 can be added to the system which can force the second pressure regulation system 710b to remain open. This attachment can be a filter to remove bacteria to sterilize air, an infusion cannula or a syringe needle. This opening of the second pressure regulation system 710b causes gas within the mixing chamber 510b to reach ambient pressure. Once sufficient time has elapsed for the gas to reach ambient pressure, the user can then set the activation system 210b to the first or "closed" position thereby unlocking the measurement control system 110b. The user can then manually expand the volume of the mixing chamber 510b to the injectable volume. In some embodiments, the measurement control system 210b can stop expansion of the volume of the mixing chamber 510b once the injectable volume is reached. Once the third phase is complete, the attachment can be removed such that the second pressure regulation system 710b can isolate the mixed gas from the surrounding atmosphere to reduce or prevent dilution of the mixed gas.

One significant advantage of the operation of the apparatus 10b is that the entire process can be performed by a single individual within the sterile field. Furthermore, the process is substantially automated such that the user need only set the measurement control system 210b to a proper setting and the apparatus 210b will automatically perform a substantial majority of the remaining steps. Additionally, the steps automatically performed by the apparatus 10b are those which can normally be most-prone to error such as measuring proper volumes to achieve a desired concentration thereby significantly reducing the risk of obtaining an incorrect concentration of gas in the injectable volume. Inadvertent dilution of the gas with the surrounding atmosphere at the conclusion of the second and third phases of the operation can be reduced or prevented with the incorporation of the second pressure regulation system 710b.

In other embodiments, a fewer or greater number of phases of operation can be performed. In some embodiments, only a single phase of operation can be performed. For example, the pressurized chamber 410a can contain a gas at a pre-set concentration level. During the single phase of operation, the user can activate the apparatus 10b such that a gas or fluid flows from the pressurized chamber 410a and into a second chamber, such as the mixing chamber 510a, until the chamber reaches a configured volume. The gas or fluid can also be expelled or bled off using a pressure regulation system until a desired pressure is achieved within the chamber. After expelling the gas, the apparatus 10b can be ready for use. As should be apparent to one of skill in the art, in such an embodiment, little to no mixing may in fact be performed.

System Overview

Figure 3:
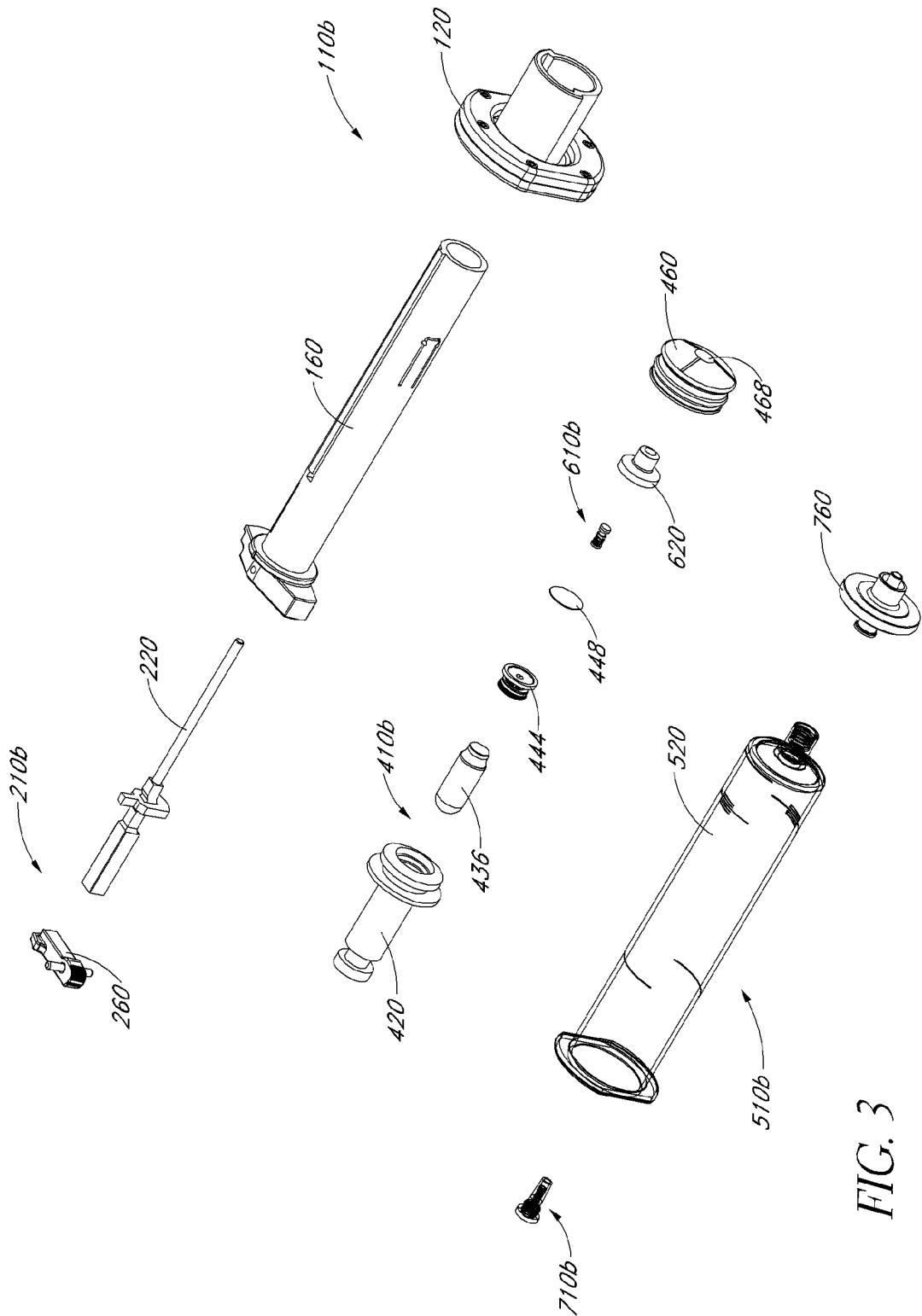
FIG. 3 is an exploded view of the components of the second embodiment of a gas mixture apparatus.

With reference to FIG. 3, components of an embodiment of a gas mixture apparatus 10b are shown which comprise a measurement control system 110b, an activation system 210b, a pressurized chamber 410b, a mixing chamber 510b, a first pressure regulation system 610b, and a second pressure regulation system 710b. The measurement control system 110b can comprise a metering dial 120 and a plunger body 160 which can be inserted into the metering dial 120. The activation system 210b can comprise an actuation rod 220 and activation switch 260. The activation system 210b can be operatively coupled to the measurement control device 110b to control the operation of the gas mixture apparatus 10b. The activation system 210b can be inserted into the plunger body 160.

The pressurized chamber 410b can be comprised of a housing 420, a canister 436 containing a gas, a release mechanism 444 to release the gas contained within the canister 436, a filter 448 to reduce the amount of non-gas or bacteria material flowing out of the housing 420, and a plunger seal 460. The mixing chamber 510b can be comprised of a syringe body 520. The first pressure regulation system 610b can comprise a valve body and associated valve components. The second pressure regulation system 710b can also comprise associated valve components.

Measurement Control System and Activation System

Figure 4:
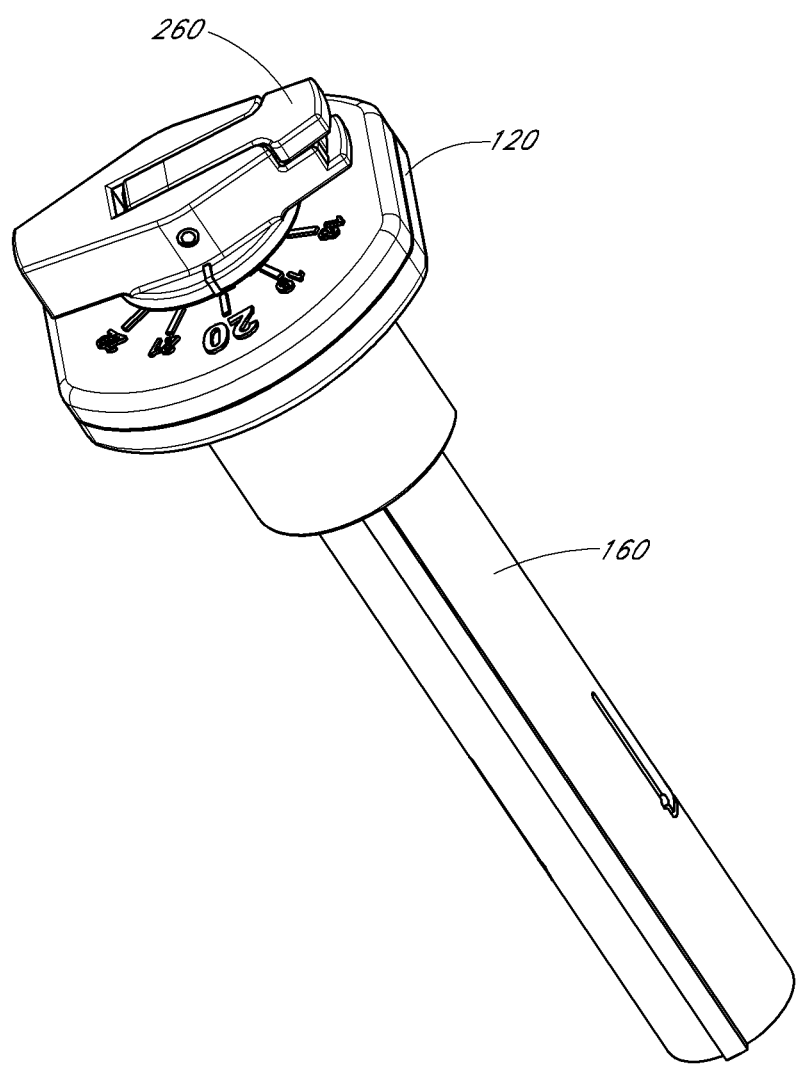
FIG. 4 is a perspective view of a measurement control system and activation system of the second embodiment of a gas mixture apparatus.

With reference to FIG. 4, an embodiment of a combined measurement control system 110b and activation system 210b is shown. The measurement control system 110b can comprise a metering dial 120 and a plunger body 160. The activation system can comprise an actuation rod 220 (shown in FIG. 7) and an activation switch 260.

Figure 5B:
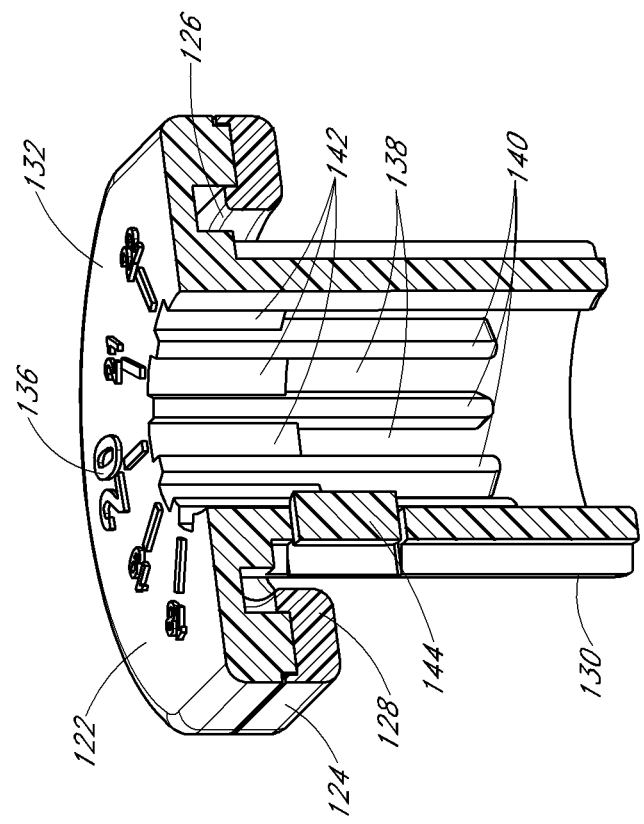
FIG. 5B is a sectional view of a metering dial of the measurement control system of FIG. 4.
Figure 5A:
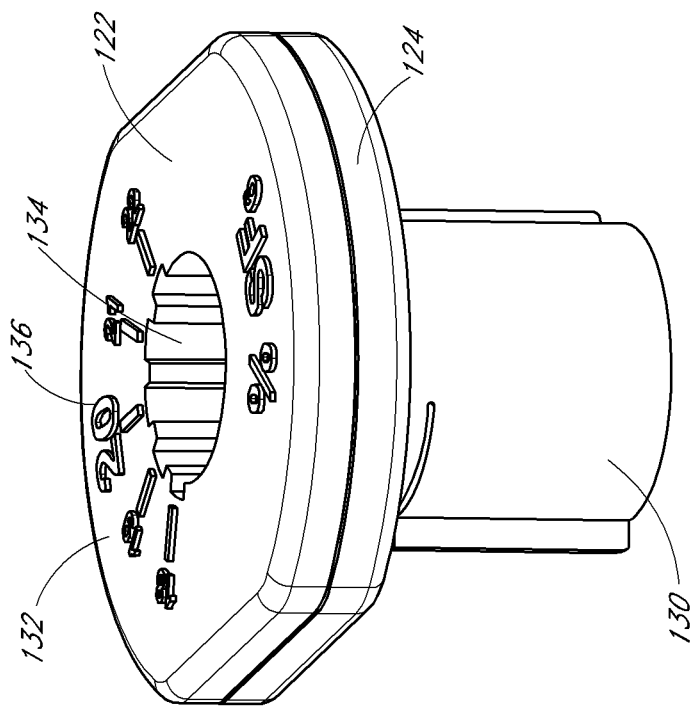
FIG. 5A is a perspective view of a metering dial of the second embodiment of a gas mixture apparatus.

With reference to FIGS. 5A and 5B, an embodiment of a metering dial 120 of the gas mixture apparatus 10b is shown which is configured to allow a user of the apparatus 10b to selectively vary the concentration of an injectable volume. The metering dial 120 is comprised of at least two structural components—a metering body 122 and a metering cap 124 which can be coupled to the metering body 122 so as to allow the metering dial 120 to be reversibly attached to another component of the apparatus 10b. This can advantageously facilitate assembly of the apparatus and, in some embodiments which are reusable, can facilitate disassembly for resterilization. In some embodiments, the metering cap 124 can be reversibly attached to the metering body 122 using fasteners such as screws, rivets, clips, and other fastening mechanisms known in the art. Attachment of the metering cap 124 to the metering body 122 can form an annular slot 126 and an annular lip 128 such that the metering dial 120 can be attached to another component of the apparatus 10b. For example, the annular slot 126 and annular lip 128 can correspond to a flange 526 located on the syringe body 520.

The metering body 122 can have a generally cylindrical member 130 with a flange 132 at the top end and a channel 134 substantially centered on the cylindrical member 130 and running throughout the entire meter body 122. Since the meter body 122 is configured to control the concentration of the gas in the injectable volume, the meter body 122 can include metering indicators 136 along a surface viewable by a user of the apparatus 10b in a fully assembled state. In the illustrated embodiment, the metering indicators 136 are located on a top surface of the flange 132 although any location which can be viewed by the user can be used. The metering indicators 136 can provide the user of the device with information regarding the operation of the apparatus 10b. In the illustrated embodiment, the metering indicators 136 show a range of numbers from 18, 19, 20, 21, and 22 corresponding to concentrations of sulfur hexafluoride ($SF_6$) which would be produced in the injectable volume if the apparatus 10b is activated. As should be apparent to one of skill in the art, the ranges used can depend upon the gas used and the application for the gas. Furthermore, in some embodiments, this range can be further divided to provide enhanced control over the desired concentration.

The metering body 122 can have slots 138, rails 140, and variable stops 142 corresponding to the metering indicators 136. In the illustrated embodiment, the metering body 122 has five separate slots 138 located along an inner surface of the channel 134 which correspond to the five integer values stated above. In other embodiments, the metering body 122 can have fewer or greater slots than the number of values provided by the metering indicators 136.

Corresponding with each of these slots 138 are variable stops 142 which extend inwardly from the slots 138. As illustrated above, these variable stops 142 can extend from the top surface of the flange 132 to a set distance towards the bottom end of the tubular body 130. In some embodiments, the variable stops 142 need not extend from the top surface but instead are minor protrusions at set distances towards the bottom end of the cylindrical member 130. These variable stops 142 are configured to interact with components contained in the plunger body 160 such as a latch 228, or the plunger body 160 itself to control the expansion volume of the mixing chamber 510b during a first and second phase of operation by limiting the rearward extension of the plunger body 160 during these phases (see FIG. 2B). As such, the variable stops 142 extend different distances depending upon the concentration to which the stop 142 corresponds. For example, a concentration of 21 percent extends a lesser distance than a concentration of 20 percent. As such, when a concentration of 21 percent is chosen, the plunger body 160 can be allowed to extend rearwardly a greater distance thereby allowing a greater expansion of the mixing chamber 510b during the first phase of operation. Therefore, as should be apparent, the variable stops 142 are used to control the first expansion volume of the first phase of operation.

On both sides of slots 138 are rails 140 which extend inward from an inner surface of the channel 134. In some embodiments, the rails 140 extend inwardly from the inner surface of the channel 134 a greater distance than the variable stops 142. The rails 140 can be configured to prevent the apparatus 10b from switching to a different concentration value once the apparatus 10b has been activated. This can be particularly important in applications where a specific concentration of gas can be necessary and any minor change in this value can have significantly adverse effects. In the illustrated embodiment, the rails 140 are configured to substantially reduce the likelihood that the plunger body 160 will rotate to a different variable stop 142 during at least the first two phases of operation. In certain embodiments, these rails can be removed if a constantly variable metering device is desired. In such an embodiment, the variable stop 142 could instead have a ramp shape rather than have multiple steps.

Metering body 122 can additionally include a ratchet pawl 144 along an inner surface of channel 134 which extends inwardly toward the center of the channel 134. The ratchet pawl 144 can be hinged and configured such that the ratchet pawl 144 is movably deformable and provides resistance during deformation. This ratchet pawl 144 can correspond to features located on the plunger body 160 to facilitate proper orientation with respect to the selected concentration. Such a mechanism can additionally provide tactile feedback to a user of the device indicating that the proper alignment has been achieved. This tactile feedback can advantageously reduce the likelihood of activation in an improper orientation. Other types of feedback mechanisms and alignment mechanisms can also be used.

Figure 6:
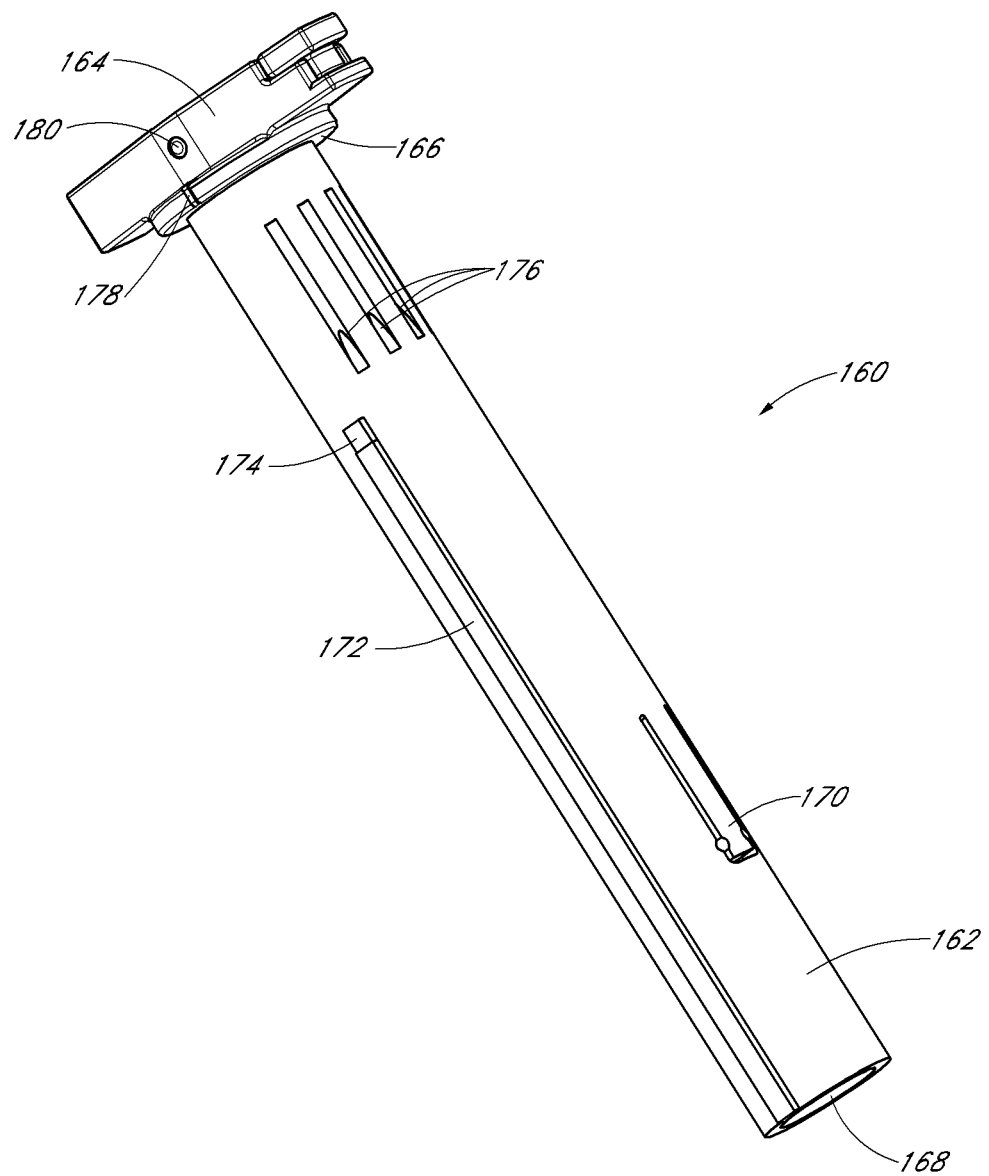
FIG. 6 is a perspective view of a plunger body of the measurement control system of FIG. 4.

With reference to FIG. 6, an embodiment of a plunger body 160 is shown which comprises a generally tubular frame 162, a handle 164 at one end of the plunger body 160, a selector ring 166 located therebetween, and a channel 168 centered on the tubular frame 162 and running throughout the entire length of the plunger body 160. The tubular frame 162 is configured to be slidably translatable and partially slidably rotatable within the channel 134 of the metering dial 120. The tubular frame 162 has a retention mechanism 170 in the form of a clip which is hingedly attached to the tubular frame 162. The retention mechanism 170 can be configured to retain a component such as a housing 420 of the pressurized chamber 410b. The retention mechanism 170 advantageously allows the component to be attached without the use of tools thereby facilitating the process of assembling the entire device. Additionally, the retention mechanism 170 can also be configured such that the component can be removed from the tubular frame 162 thereby allowing the apparatus 10b to be reused or, in other embodiments which allow for reuse of the apparatus 10b, facilitating the process of resterilization if such a process is used for the device. Other types of retention mechanisms can also be used in lieu of the clips shown in the illustrated embodiment and can include fasteners such as screws.

Tubular frame 162 can additionally comprise a guard 172 which extends outward from the outer surface of the tubular frame 162. The guard 172 can run from the bottom end of the tubular frame 162 to a distance toward the top end of the tubular frame 162. The guard 172 is configured to fit within the slots 138 and rails 140 located along the inner surface of the channel 134 of the metering body 122. As such, the guard 172, when positioned between the rails 140, can prevent the plunger body 160 from rotating. This advantageously can prevent the plunger body 160 from moving to a different variable stop 142 after commencing the first phase of operation and thereby reduce the risk of an improper concentration in the injectable volume. The guard 172 is preferably sized such that, when the plunger body 160 is fully inserted, the guard 172 is only slightly below the rails 140 such that the plunger body 160 can rotate freely to different concentration values during the initial phase of operation (see FIG. 2A). However, because the guard 172 is only slightly below the rails 140, once extended a short distance, the guard 172 can become locked within the selected rail 140. This positioning advantageously allows the guard 172 to lock shortly after activation of the apparatus 10b. Furthermore, the guard 172 preferably extends outward from the tubular frame 162 only a sufficient distance such that it can contact the rails 140 but not enough such that it contacts the variable stops 142 located between the rails 140. This can therefore allow the guard 172 to not be interfered by the variable stops 142 during operation.

Tubular frame 162 can additionally comprise a latch aperture 174 configured to allow a latch 228 located on the activation rod 220 to protrude outward from the tubular frame 162. The latch aperture 174 is preferably centered just above the top-most portion of the guard 172. As will be discussed in detail below, in a first or "closed" position, the latch 228 can not extend beyond the guard 172 and thus would not contact a variable stop 142 (see FIG. 8A). When in a second position, the latch 228 can extend outward from the tubular frame 162 beyond the guard 172 such that the latch 228 can contact the variable stops 140 thereby preventing further extension of the plunger body 160 while the latch is in the second position (see FIG. 8B). In some embodiments, the latch aperture 174 can be placed such that, if the plunger body 160 is improperly oriented within the metering dial 120 during an initial phase of operation (shown in FIG. 2A), the latch 228 can be prevented from extending outward into the second or "open" position by a rail 140 of the metering dial 120. This can advantageously prevent the apparatus 10b from activating when improperly oriented.

Tubular frame 162 can additionally include ratchet slots 176 in the form of cut-outs located along its outer surface. The ratchet slots 176 are configured to receive the ratchet pawl 144 of the metering body 122 thereby providing a mechanism for ensuring that the plunger body 160 is properly oriented within the metering body 122 by providing resistance against rotation when the pawl 144 is received within one of the ratchet slots 176. Furthermore, advantageously, at each point where the ratchet pawl 144 is received within the ratchet slots 176, a user of the apparatus 10b can also receive tactile feedback when the plunger body 160 is properly oriented within the metering body 122.

Selector ring 166 can be an annular protrusion extending from the outer surface of the tubular frame 162. The selector ring 166 can additionally include a selector indicator 178 which can take the form of a minor protrusion located on the selector ring 166. Selector indicator 178 can correspond to the metering indicators 136 located on the metering body 122 to indicate the concentration level that will be obtained when the plunger body 160 is oriented in that position. Such a system can advantageously provide a user of the device with easily viewed information regarding the selected concentration level. The selector indicator 178 can advantageously be colored to facilitate use of the apparatus 10b.

The handle 164 can extend in two opposite directions in a radial direction from the longitudinal axis of the tubular frame 162. Handle 164 can be shaped such that a user of the apparatus 10b can contact the handle 164 and use the handle to either further extend the plunger body 160 rearward and out of the apparatus 10b or further depress the plunger body 160 frontward into the apparatus 10b. Handle can additionally include a pin aperture 180 for receiving a coupling mechanism for the activation switch 260. The activation switch 260 can thereby rotate about the coupling mechanism in order to operate the actuation rod 220 located within the plunger body 160.

Figure 7:
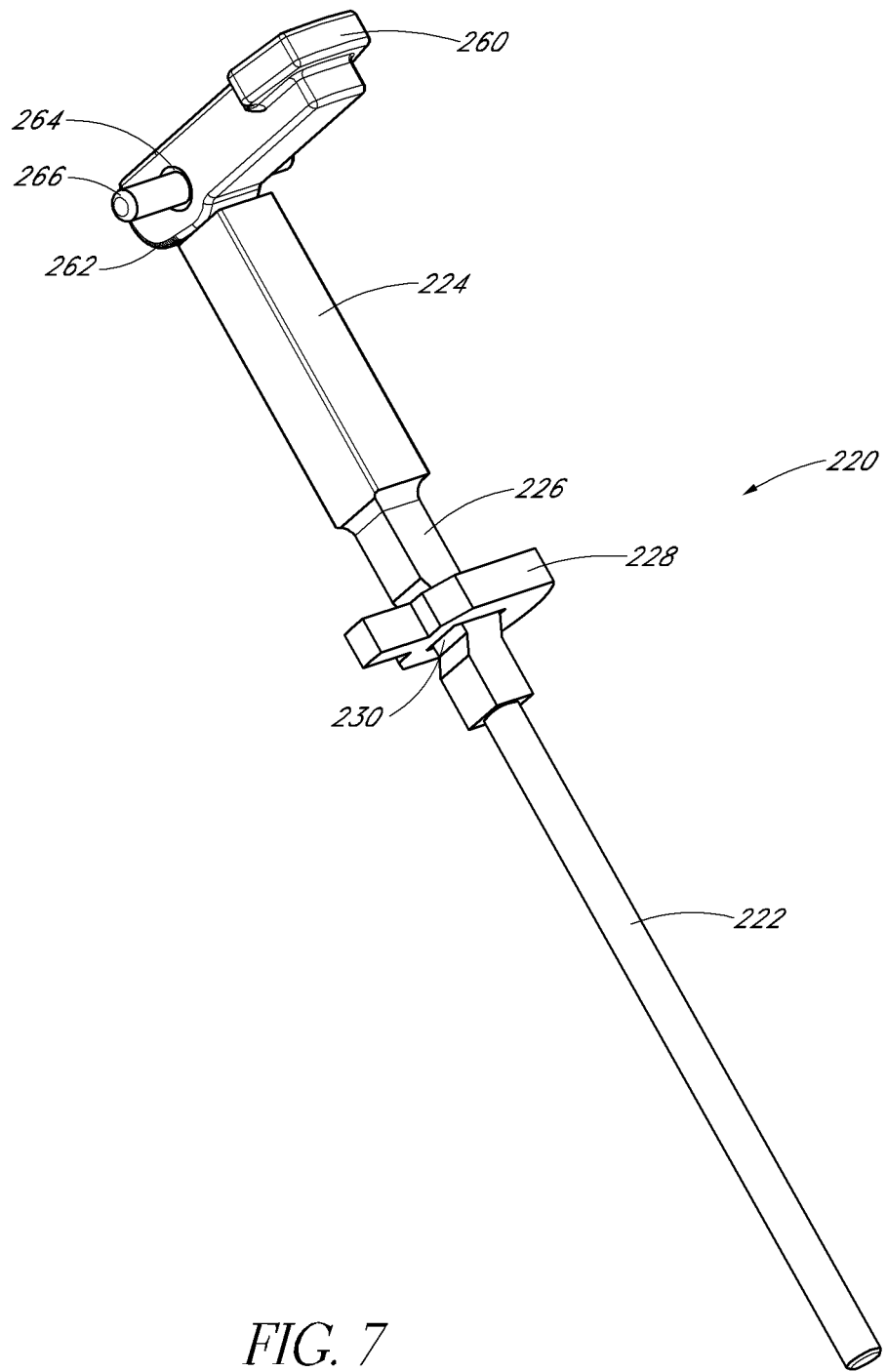
FIG. 7 is a perspective view of the activation system of FIG. 4.

With reference to FIG. 7, an embodiment of an activation system 210b is shown which comprises an actuation rod 220 and an activation switch 260. The actuation rod 220 has a generally elongate body with an actuator pin 222 at a first end, an actuator stem 224 at a second end, and a latch movement portion 226 located in an intermediate portion. The actuator pin 222 is configured to be received within a housing 420 of the pressurized chamber 410b and activate the release of gas contained therein when in a second or "open" position. The actuator stem 224 is configured to abut and follow the contoured surface 262 of the activator switch 260. The actuator stem 224 is also preferably shaped such that the cross-sectional profile matches the cross-sectional profile in a top portion of the channel 169 (as shown in FIG. 8) located near the handle 164 of the plunger body 160. Preferably, the cross-sectional profile is not substantially circular such that the actuator rod 220 is substantially prevented from rotating within the channel 168 of the plunger body 160. The latch movement portion 226 is shaped such that the latch 228 is translated when the latch 228 slidably translates along the latch movement portion 226 of the actuation rod 220. As such, the latch 228 has an aperture 230 which has a cross-sectional shape similar to that of the cross-sectional shape of the latch movement portion 226.

The activator switch 260 is configured to translate the actuator rod 220 through the plunger body 160 and through the housing 420 of the pressurized chamber 410b to activate the release of gas contained therein. As such, the activator switch 260 can be a cam with a contoured profile 262 along the surface configured to contact the actuator stem 224. Activator switch can also have an aperture 264 configured to receive a pin 266 such that the activator switch 260 can rotate about the pin 266. In the illustrated embodiment, the activator switch 260 is shown in a first or "closed" position. In this first position, the distance between the pin 266 and the contoured surface 262 in contact with the actuator stem can be a reduced distance such that the actuator rod remains in a first or "closed" position. However, when rotated about the pin 266 to a second or "open" position, the distance between the pin 266 and the contoured surface 262 in contact with the actuator stem 224 can be an increased distance thereby translating the actuator rod 220 to a second or "open" position further into the housing 420 of the pressurized chamber 410b. As will be discussed in greater detail with respect to FIGS. 10 and 11 below, movement into the second or "open" position can be configured to release gas in the pressurized chamber 410b. The activator switch 260 can preferably be any type of switch that can remain in a first or second position without the user needing to maintain the switch in that position. In the illustrated embodiment, a rotating lever is used. Other switches can also be used such as a screw, latch, spring loaded pin, or any other switch known in the art.

Figure 8A:
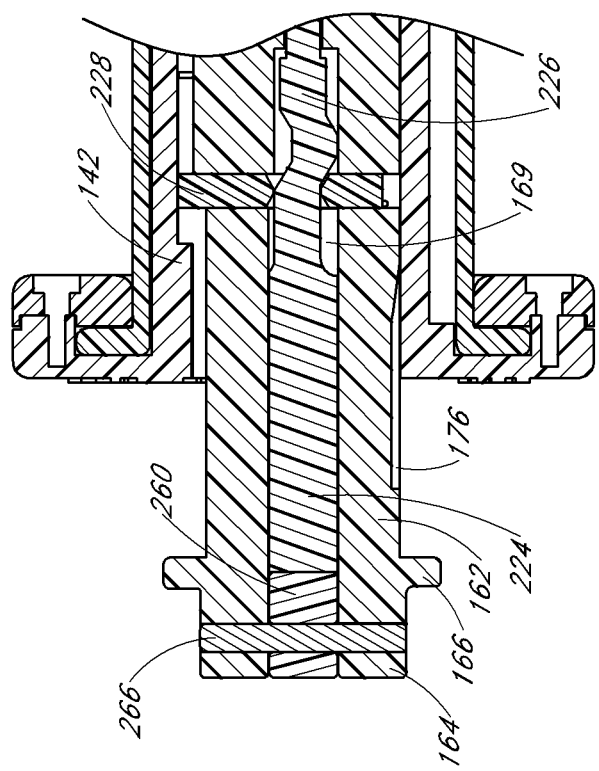
FIG. 8A is a sectional view of the measurement control system and activation system of FIG. 4 in a first or "closed" position.
Figure 8B:
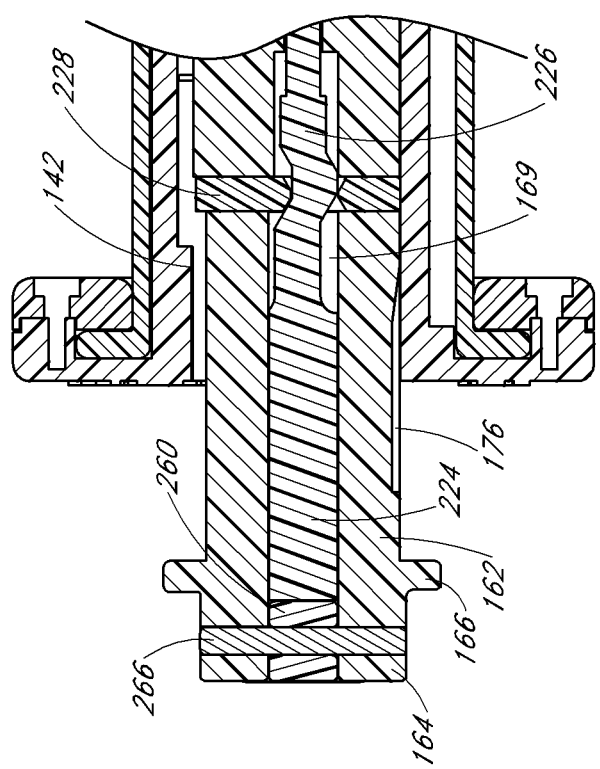
FIG. 8B is a sectional view of the measurement control system and activation system of FIG. 4 in a second or "open" position.

With reference to FIGS. 8A and 8B, an illustration of the operation of the activation system 210b is shown which includes some components of the measurement control system 110b and the activation system 210b. As shown here, the latch 228 is contained within the latch aperture 174 such that the latch cannot translate toward a front end or rear end of the plunger body 160. As such, when the actuator rod 220 translates in a frontward or rearward direction, the latch 228 must follow the profile of the latch movement portion 226 of the actuator rod 220. As such, this provides the advantage of coupling movement of the latch 228 in the second position when the activator switch 260 and thus the actuator rod 220 are in a corresponding second position. Furthermore, because movement of the latch 228 is coupled with movement of the other activator switch 260 and actuator rod 220, if the latch 228 is prevented from moving into the second position, the activator switch 260 and activator rod 220 are also prevented from moving into the second position. Note that, as described above, while in the second or "open" position, the latch 228 can protrude from the plunger body 160 thereby restricting extension of the plunger body 160 as shown in FIG. 8B.

Pressurized Chamber and First Pressure Regulation System

Figure 9:
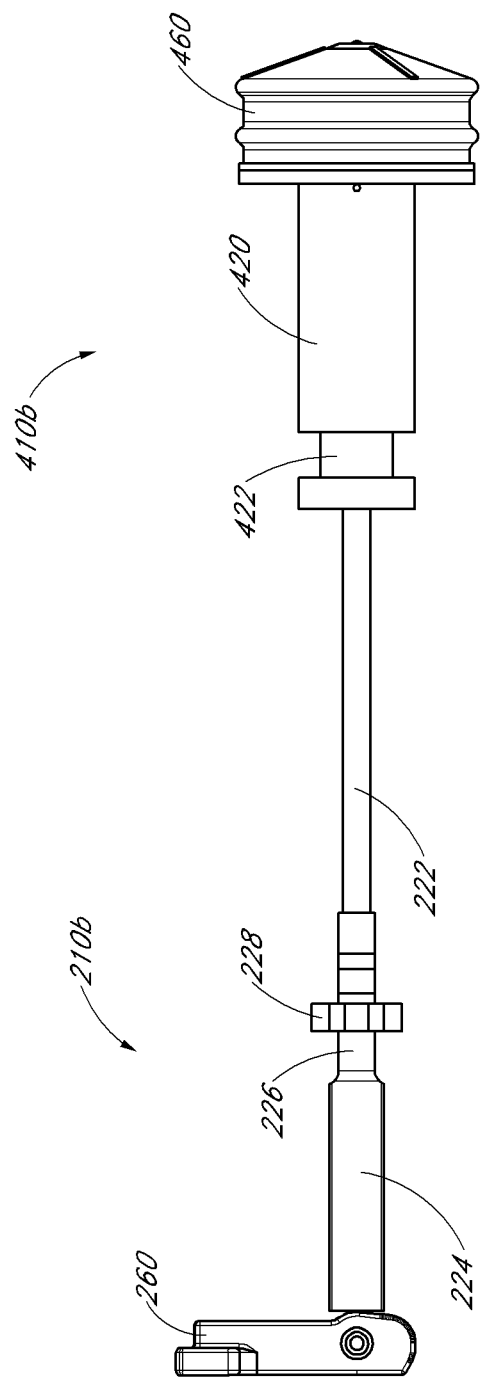
FIG. 9 is a side view of an embodiment of an activation system, pressurized chamber, and first pressure regulation system of the second embodiment of a gas mixture apparatus.

With reference to FIG. 9, an embodiment is shown including some components of both the activation system 210b, the pressurized chamber 410b of the mixing system 310b, and the first pressure regulation system 610b of the mixing system 310b. As illustrated, the pressurized chamber 410b can have a housing 420 with an annular slot 422 located near a first end of the housing 420. The annular slot 422 can be configured to receive the retention mechanism 170 located on the plunger body 160. Housing can also have a plunger seal 460 located at a second end of the housing 420. The plunger seal 460 is configured to provide an airtight seal for defining the mixing chamber 510b.

Figure 10:
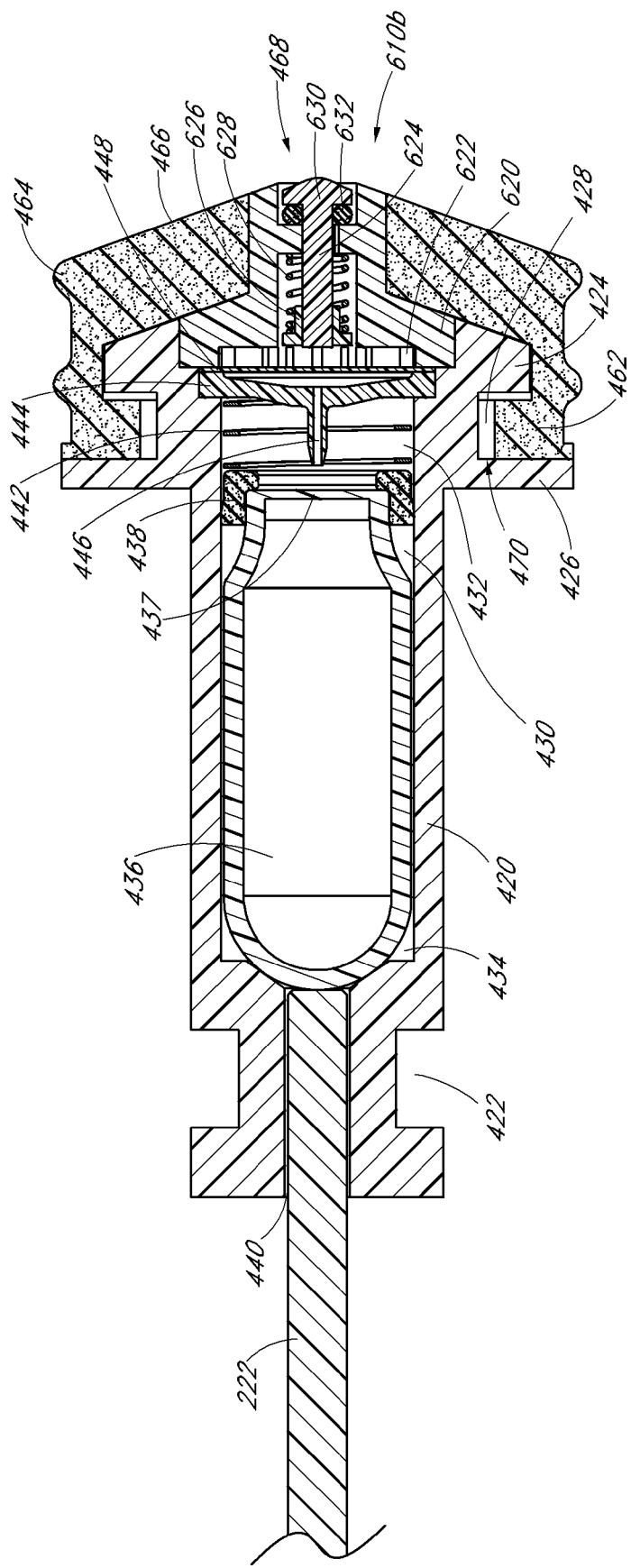
FIG. 10 is a sectional view of the activation system, pressurized chamber, and first pressure regulation system of FIG. 9 in a first position.

With reference to FIG. 10, which is a sectional view of the pressurized chamber 410b and the first pressure regulation system 610b. The housing 420 has a generally cylindrical body with an annular slot 422 located at the first or rearward end and a conical or frusto-conical surface 424 located at the second or frontward end corresponding to the shape of the plunger seal 460. Housing 420 can additionally be shaped such that it has an annular protrusion 426 and an annular slot 428 configured to receive a lip 462 of the plunger seal 460. This configuration advantageously ensures that the plunger seal 460 remains connected to the housing 420 and forms a seal to prevent the leakage of any gas contained in the housing body 420. It can be preferable that the lip 462 of the plunger seal 460 fit snugly within the annular slot 428 of the housing 420 to provide an enhanced seal. An interior space 430 is substantially enclosed by the housing 420 and can be separated into a first separate portion 432 and a second separate portion 434. Contained within the second separate portion 434 of the housing 420 can be a third separate portion in the form of a structural unit such as a canister 436. This canister can contain the gases for mixing into the mixing chamber 510*b*. Provision of the gases in a canister is advantageous as it facilitates manufacturing of the apparatus 10*b* as it can allow the canisters to be manufactured separately from other components of the pressurized chamber 410*b*. In some embodiments where the apparatus 10*b* is reusable, cartridges can be replaced.

The canister 436 has a first or rearward end in contact with the actuator pin 222 and a sealed second or frontward end 437. At one end of the canister 436 is a seal 438 which substantially reduces leakage of any gas from the first separate portion 432 to the second separate portion 434. This advantageously reduces the likelihood of gases from leaking out of the actuator aperture 440 and out of the apparatus 10*b*.

The housing can also include a biasing mechanism 442, such as a spring, which exerts a force on the seal in a direction away from the second end of the housing 420. In the illustrated embodiment, the biasing mechanism 442 is located in the first separate portion 432. This reduces the likelihood of the canister 436 moving into the first separate portion 432 and potentially releasing the gas contained therein without having been activated by the user. Furthermore, biasing mechanism 442 can also provide a counterforce against activation such that a user can not accidentally activate the device. It is preferable that the biasing mechanism 442 be configured to exert a sufficient force such that, after the first and second phases of operation are complete and the activation switch 160 is returned to a first or "closed" position, the biasing mechanism 442 exerts sufficient force such that actuator rod 220 is returned to its first or "closed" position thereby causing the latch 228 to return to its first or "closed" position. Once latch 228 returns to its first or "closed" position, the extension of the plunger body 160 is no longer limited and the third phase of operation can commence. If the biasing mechanism 442 does not exert sufficient force on the actuator rod 220, entering into the third phase of operation could be made significantly more difficult.

Housing can also have a release mechanism 444, such as a needle or a pilot tip as illustrated in this embodiment of the apparatus 10*b*, which can be configured to puncture the sealed second end 437 of the canister 436 to release gas into the first separate portion 432 through the release mechanism 444 due to a channel 446 running axially through release mechanism 444. Due to the high pressure in the first separate portion 432, the first pressure regulation system 610*b* can open allowing the gas to escape to the front of the plunger seal 460 and into the mixing chamber 510*b*. In some embodiments, a filter 448 can be placed along the flow path such that there is a reduced likelihood of foreign materials entering into the mixing chamber 510*b*. This can be particularly important when the gas can be placed into areas highly sensitive to the presence of foreign materials such as bodily cavities. The presence of foreign materials can cause infection or other harm. In some embodiments, the filter 448 can be configured to filter out bacteria to sterilize the air.

Plunger seal 460 is configured to partially define the injectable volume of the mixing chamber 510*b* by creating a seal for the mixing chamber 510*b*. Plunger seal 460 can have a generally cylindrical body with annular protrusions 464 configured to contact an inner surface of the mixing chamber 510*b* and a conical or frustoconical face 466 at a frontward end. The frustoconical face 466 can additionally comprise an aperture 468 centered about the cylindrical body configured to receive components of the first pressure regulation system 610*b*. Furthermore, the body can also have an opening 470, defined by the lip 462, on the rearward end configured to receive the housing 420.

With continued reference to FIG. 10, an embodiment of the first pressure regulation system 610*b* is shown in a first or "closed" position. The first pressure regulation system 610*b* can comprise a valve body 620 comprising multiple apertures 622 at one end, a valve stem 624 running through the valve body 620 with a seat 626 at a rear end configured to contact the biasing mechanism 628 and a head 630 at a front end configured to contact a sealing ring 632. During operation, the biasing mechanism 628 can exert a biasing force against the seat 626 in a rearward direction such that the head 630 is biased against the sealing ring 632 and valve body 620 thereby reducing or preventing the flow of gas through the valve body 620 and ultimately into the mixing chamber 510*b*. Due to the orientation of the biasing mechanism 628, the first pressure regulation system 610*b* remains closed until pressure within the pressurized chamber 410*b* exceeds a threshold value. This threshold value can be configured by changing the amount of force necessary to compress the biasing mechanism 628.

Figure 11:
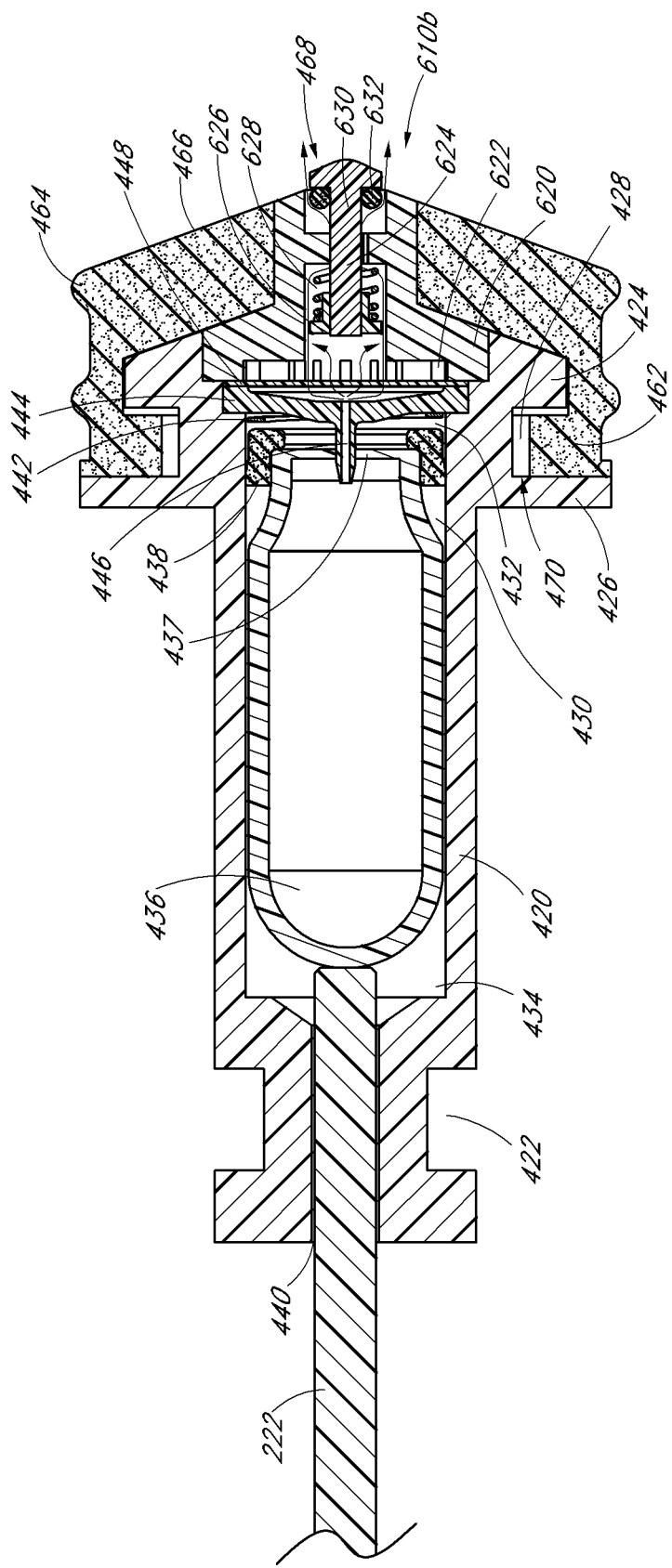
FIG. 11 is a sectional view of the activation system, pressurized chamber, and first pressure regulation system of FIG. 9 in a second position.

With reference to FIG. 11, an embodiment of the first pressure regulation system 610*b* is shown in an "open" position during the first and second phase of operation. During these phases, pressure within the pressurized chamber 410*b* can exceed the pressure within the mixing chamber 510*b*. In some preferred embodiments, the difference in pressure is substantial. Due to this pressure differential, sufficient force is placed upon the valve components causing the biasing mechanism 628 to be overcome thereby allowing gas to flow out of the valve body 620 and into the mixing chamber 510*b*.

This configuration for the first pressure regulation system 610*b* is advantageous due to the multiple phases of operation of the apparatus 10*b*. During the first and at least part of the second phase of operation, the pressure differential causes the valve to remain open. However, once the pressure differential is insufficient to overcome the threshold value, the valve remains in a closed position preventing any additional gas from flowing into the mixing chamber and potentially disrupting the calculated pressures/concentrations.

Figure 12:
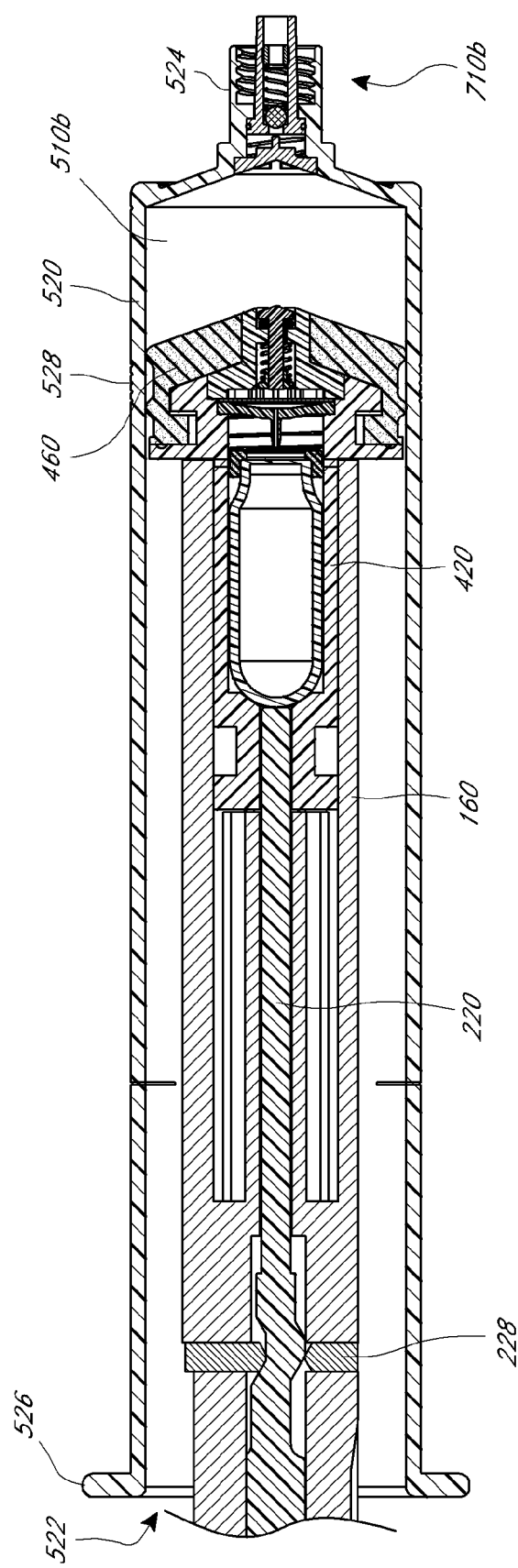
FIG. 12 is a sectional view of components including a mixing chamber and second pressure regulation system of a second embodiment of a gas mixture apparatus.

With reference to FIG. 12, an embodiment of a mixing chamber 510*b* is shown comprising a syringe body 520, a second pressure regulation system 710*b*, and various components of the above-mentioned systems. Syringe body 520 has a cylindrical body, an aperture 522 at the rear end, and a threaded nozzle 524 at the front end. Syringe body also has flange 526 configured to be engaged with the metering device 120. The mixing chamber 510*b* can be defined by the inner walls of the syringe body 520 and the plunger seal 460. Furthermore, the syringe body can include indicators 528 along its outer surface corresponding to a chosen concentration. These indicators 528 can advantageously provide visual confirmation to the user of the selected concentration.

Figure 13:
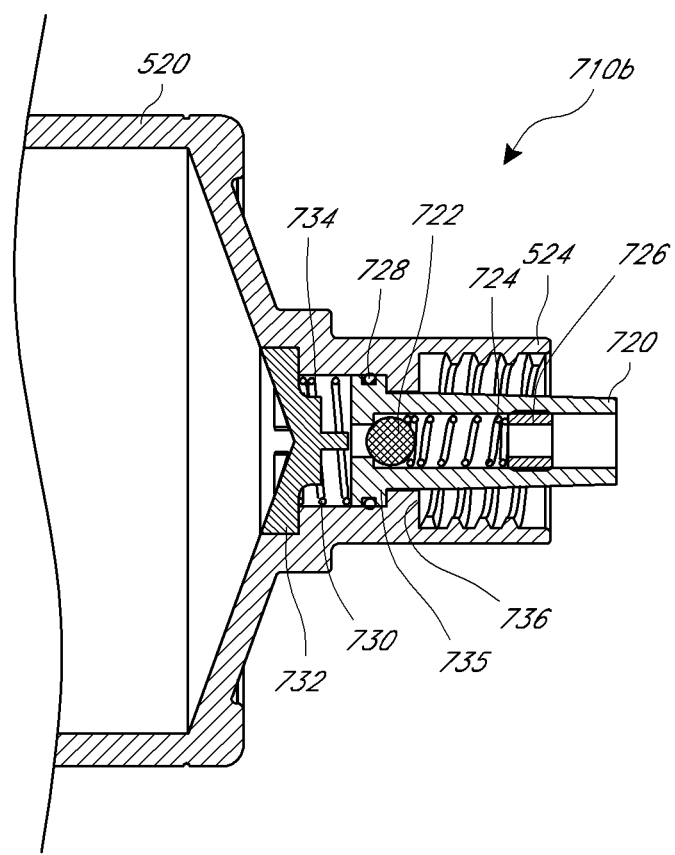
FIG. 13 is an enlarged sectional view of the mixing chamber and second pressure regulation system of FIG. 12.

With reference to FIG. 13, an embodiment of the second pressure regulation system 710b is shown comprising a valve body 720 which can include a ball 722, a biasing mechanism 724, a seat 726, and a sealing mechanism 728. The second pressure regulation system 710b can also comprise a second biasing mechanism 730 and a pin actuator 732. The valve body 720 can be translatable within the interior space 734 near the nozzle 524 of the syringe body 520. In some embodiments, due to the second biasing mechanism 730, the valve body 720 is translated such that a flange 735 of the valve body 720 is pressed against the inner lip 736 of the nozzle 524. Furthermore, biasing mechanism 724 can seal flow through the valve body 720 until a sufficient force is placed on the ball 722 to overcome the biasing force. This can occur when the pressure differential between the mixing chamber 510b and the atmosphere is beyond a threshold value.

During operation, the second pressure regulation system 710b is opened during a first and second phase of operation due to the increased pressure contained in the mixing chamber 510b. Once the pressure differential is insufficient to cause valve body 720 to open, the second phase of operation is complete and the user can proceed to the third phase of operation.

Figure 14:
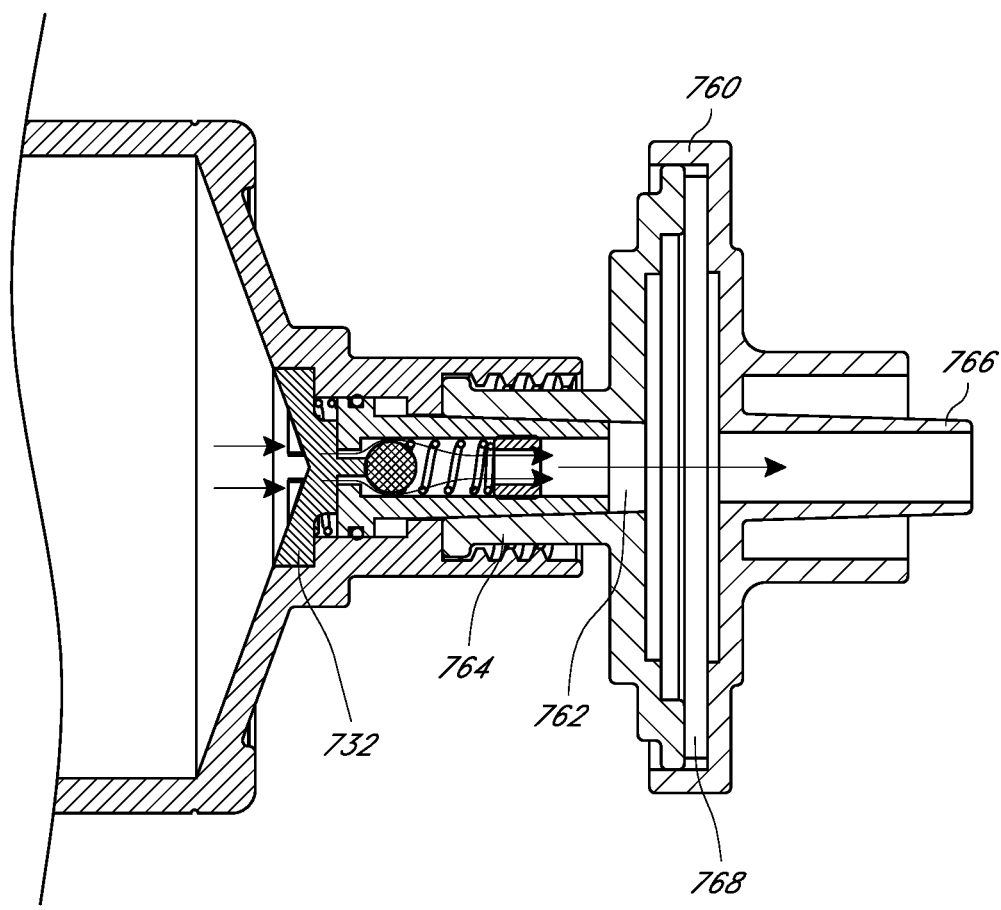
FIG. 14 is an enlarged sectional view of the mixing chamber and second pressure regulation system of FIG. 12 with an additional attachment.

With reference to FIG. 14, an embodiment of the second pressure regulation system 710b is shown with an attachment 760 comprising a filter. The attachment 760 has a first open end 762 with a flange 764 configured to engage with the threads on the interior of the threaded nozzle 524, a second open end 766, and a filter element 768 located therebetween. As such, gas can pass from the first open end 762 to the second open 766 and advantageously be filtered in the process which reduces the risk of any harmful materials enter the mixing chamber 510b. In some embodiments, the inner surface of the first open end 762 tapers when moving towards the second open end 766 such that the shape corresponds to the shape of valve body 720. As the attachment 760 is threaded into the threaded nozzle 524, the attachment 760 engages the valve body 720 and translates the valve body 720, against the biasing force of the second biasing mechanism 730 towards the rear end of the syringe body 520. This causes the ball 722 to engage the pin actuator 732 thereby causing the valve body 720 to open allowing gas within the mixing chamber 510b to reach ambient pressure. This configuration is advantageous as it allows the mixing chamber 510b to be further expanded at ambient pressure and simultaneously filtering air drawn into the mixing chamber 510b. In this position, the third phase of operation can therefore be performed. Once the third phase of operation is completed, the attachment 760 can be removed. Due to the force of the second biasing mechanism 730, the valve body 720 can be translated away from pin actuator 732 such that the valve body 720 remains closed until a user decides to inject the gas.

Embodiment of Measurement Control System and Activation System

FIGS. 15-30 illustrate additional embodiments of components of a measurement control system of the apparatus.

Figure 15A:
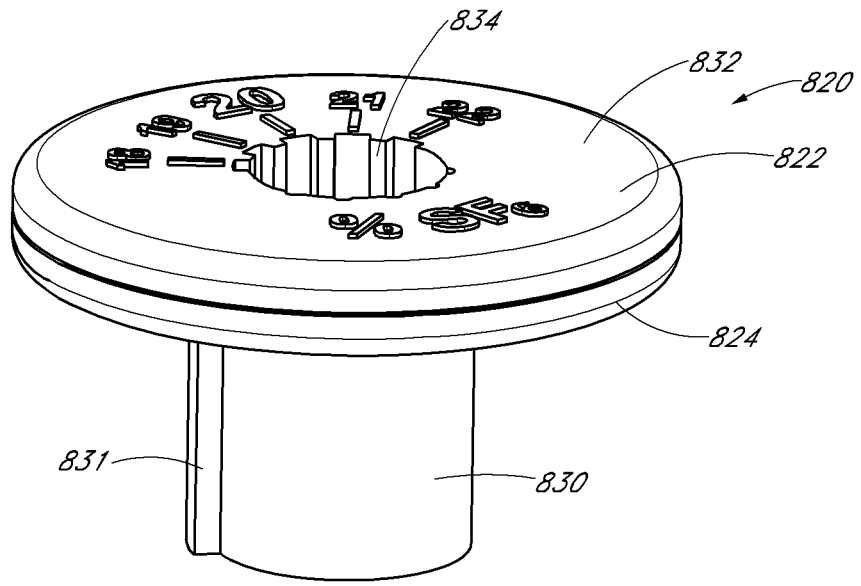
FIG. 15A is a perspective view of a metering dial of an embodiment of a measurement control system.
Figure 15B:
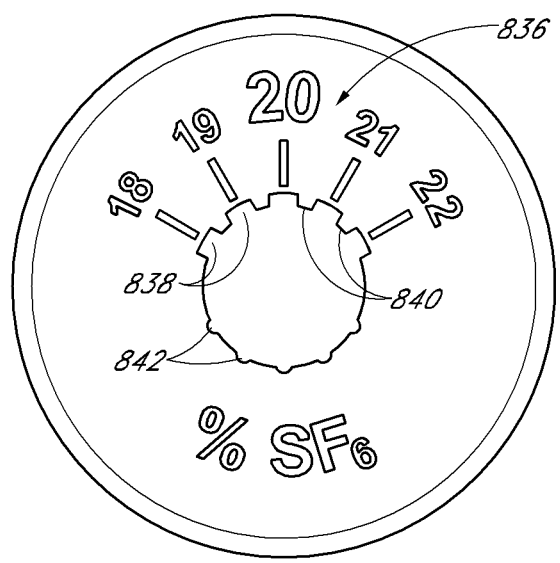
FIG. 15B is a sectional view of a metering dial of an embodiment of a measurement control system.

FIGS. 15A and 15B illustrate an embodiment of a metering dial 820 which can be configured to allow a user of the device to select a concentration of fluid for an injectable volume. Similar to other embodiments, the metering dial 820 can include two components such as a metering body 822 and a metering cap 824 which can be removably attached to the metering body 822. As with other embodiments of a metering dial and similar metering devices, such as metering dial 120, the removable attachment can advantageously facilitate the assembly of the apparatus. Furthermore, in some embodiments, the removable attachment can allow for disassembly such that the apparatus can be reduced to individual components to facilitate resterilization of some or all of the components of the apparatus. As with other embodiments, the metering cap 824 can be reversibly attached to the metering body 822 using fasteners such as screws, rivets, clips, and other fastening mechanisms known in the art. In other embodiments, the metering body 822 and metering cap 824 can be irremovably attached using devices and methods such as adhesives, welding, and the like. Such embodiments can provide an advantage of reducing the likelihood of tampering. Attachment of the metering cap 824 to the metering body 822 can form an annular slot and an annular lip such that the metering dial 820 can be attached to another component of the apparatus. In some embodiments, the annular slot and the annular lip can correspond to corresponding features, such as a flange and lip, located on a syringe on which the metering dial 820 is placed.

With continued reference to FIG. 15A and FIG. 15B, the metering body 822 can have a generally cylindrical member 830 with a flange 832 located at top portion of the metering body 822. The metering body 822 can include a channel 834 substantially centered on the cylindrical member 830 and running throughout the entire metering body 822. In some embodiments, the generally cylindrical member 830 can be sized and shaped to be received within a channel of another component of the apparatus. For example, in some embodiments, the metering body 822 can be received within a channel of a syringe to which the metering dial 820 is attached. In some embodiments, such as that illustrated in FIG. 15A, the generally cylindrical member 830 can include additional surface features, such as an increased diameter portion 831, which can potentially be keyed to the device into which it is inserted.

As with other embodiments of metering dials or similar metering mechanisms, this embodiment can also include metering indicators 836 located along a surface of the metering body 820. In this illustrated embodiment the metering indicators 836 are located on a top surface of the flange 832 although any other viewable location can be used such as, for example, along the perimeter portion of the flange 832. In the illustrated embodiment, the metering indicators 836 show a range of numbers from 18, 19, 20, 21, and 22 corresponding to concentrations of sulfur hexafluoride ($SF_6$) which can be produced in an injectable volume of the assembly. As should be apparent to one of skill in the art, the ranges used can depend upon the gas used and the application for the gas. In some embodiments this range can be further divided to provide greater precision and control over the desired concentrations.

As with other embodiments of metering dials and other metering mechanisms, the metering body 822 can have slots 838, rails 840, and variable stops corresponding to the metering indicators 836. As more clearly shown in FIG. 15B, the metering body 822 can have five separate slots 838 located along an inner surface of the channel 834 which correspond to the five metering positions 18, 19, 20, 21 and 22. In other embodiments, the metering body 822 can have fewer or greater slots than the number of values provided by the metering indicators 836. Corresponding with each of these slots 838 can be variable stops which extend inwardly from the slots 838. These variable stops can extend from the top surface of the flange 832 to a set distance towards the bottom end of the generally cylindrical member 830. As should be appreciated by one of skill in the art, the variable stops need not extend from the top surface. For example, in some embodiments, the variable stops can be protrusions at set distances towards the bottom end of the tubular body 830.

The operation of the variable stops of the illustrated embodiment of the metering dial 820 can be similar to that of other embodiments of metering dials and metering mechanisms. The variable stops can be configured to interact with components contained within the plunger body 860, such as a latch 928 or similar protruding structure, to control expansion of a chamber for an injectable volume during at least some phases of operation. In some embodiments, the variable stops can perform this task by limiting the rearward extension of the plunger body 860 during different phases. As such, the variable stops extend different distances depending upon the concentration to which the stop corresponds.

With continued reference to FIGS. 15A and 15B, both sides of slots 838 can be bounded by rails 840 which extend inwardly from an inner surface of the channel 834. In some embodiments, the rails 840 can extend inwardly from the inner surface of the channel 834 a greater distance than the stops. The rails 840 can be configured to prevent the apparatus from switching to a different concentration value once activated. In the illustrated embodiment, the rails 840 are configured to substantially reduce the likelihood that the plunger body 860 will rotate to a different variable stop during at least the first two phases of operation. In certain embodiments, the rails 840 can be removed if a constantly variable metering device is desired. In such circumstances other mechanisms can be used to prevent or otherwise significantly reduce the likelihood that a different concentration value will be chosen after the device has been activated.

As illustrated more clearly in FIG. 15B, metering body 822 can additionally include along an inner surface of the channel 834 notches, indentations, divots, recesses, or similar structures 842 located along an inner surface of the channel 834 opposite the slots 838 and rails 840. In other embodiments, the notches 842 can be located at other suitable locations on the metering dial 820. These notches 842 can correspond to features located on other components of the apparatus to form a ratcheting mechanism. For example, the notches 842 can correspond to a ratcheting member 886 (shown on FIGS. 21-23) located on the plunger body 860. As such, the ratcheting mechanism can be configured to advantageously provide a user with tactile feedback when the plunger body 860 has been rotated to a selectable concentration. As such, a user of the device can be less likely to accidentally have the plunger body 860 in an inoperable position when the gas assembly is activated. Furthermore, the ratcheting mechanism can also provide a threshold resistance against rotation from one concentration to a second concentration. In such embodiments, the ratcheting mechanism can thereby advantageously reduce the likelihood of unintentional rotation from one concentration to a second concentration. Other types of feedback mechanisms and alignment mechanisms can also be used to provide this tactile feedback.

Figure 16:
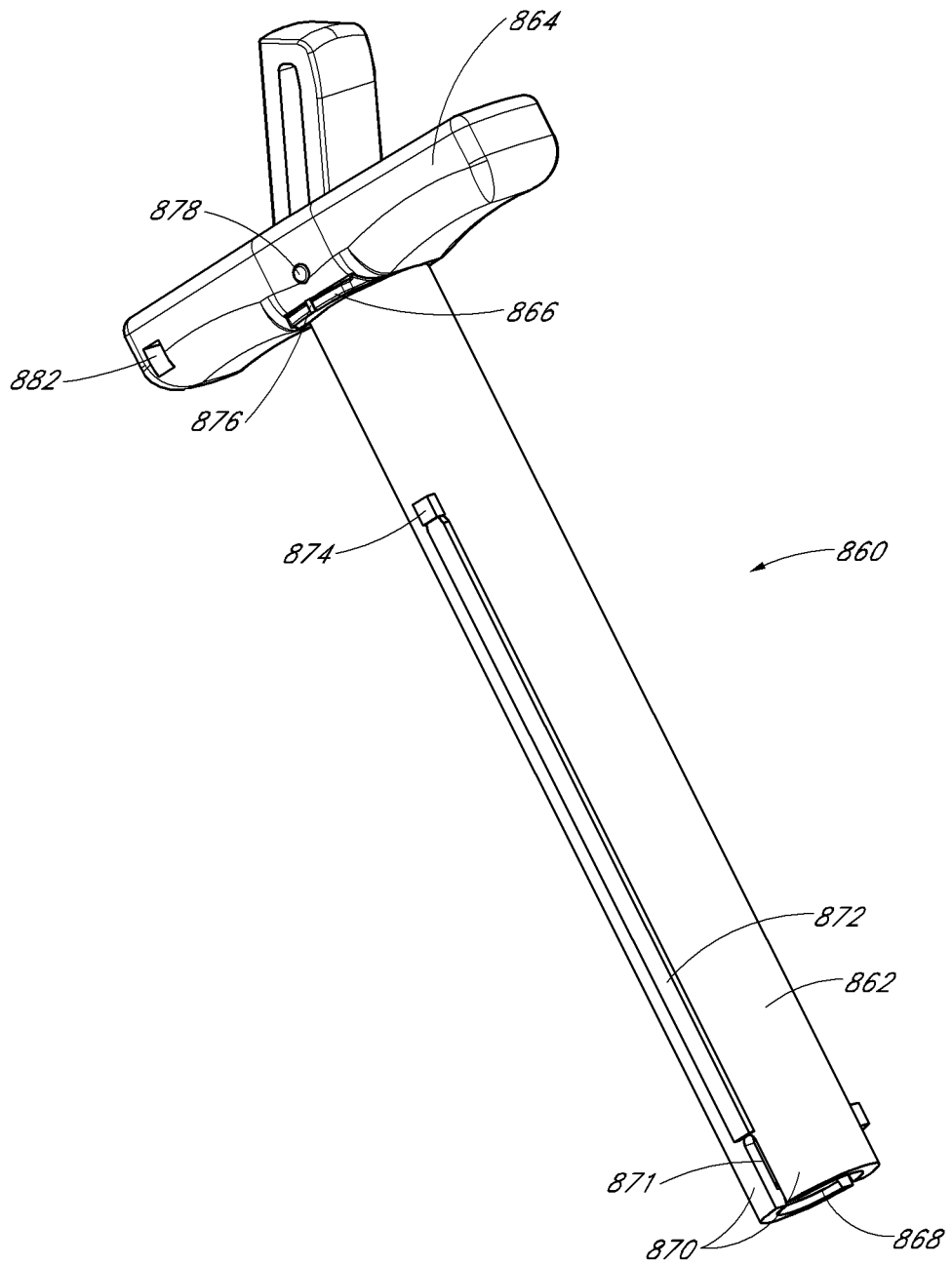
FIG. 16 is a perspective view of a plunger body of an embodiment of a measurement control system.

With reference to FIG. 16, an embodiment of a plunger body 860 is shown which can include a generally tubular frame 862, a handle 864 at one end of the plunger body 860, a selector member 866 located there between, and a channel 868 centered on the tubular frame 862 which can run throughout the entire length of the plunger body 860 or which can run throughout at least a part of the length of the tubular frame 862. The tubular frame 862 can be configured to slidably translate and slidably rotate within a channel of a metering dial.

The tubular frame 862 can include retention wings or clips 870 located at an end opposite of the handle 864. As shown in the illustrated embodiment, the retention wings 870 can be partially cylindrical protrusions separated by two or more cutouts or slits 871. As such, depending on the material used, the retention wings 870 can be bent outwardly when receiving a component within the channel 868. In some embodiments, the retention wings 870 can each include a semi-annular lip along an interior surface of the retention wings 870 which corresponds to an annular slot of a component inserted within the channel 868. For example, in some embodiments, the semi-annular lip can correspond to an annular slot 1024 located on a second housing member 1022 (see FIG. 24). As such, the retention wings 870 can allow for a snap fit assembly of multiple components of the device thereby facilitating assembly and also potentially allowing for disassembly for purposes of reuse and/or resterilization. Other fastening mechanisms and methods can also be used to connect the components to the plunger body 860 including fasteners such as screws, adhesives, welding, and other similar mechanisms and methods known in the art.

With continued reference to FIG. 16, the tubular frame 862 can include a guard 872 which can extend outwardly from the outer surface of the tubular frame 862. In some embodiments, the guard 872 can run from the bottom end of the tubular frame 862 to a distance toward the top end of the tubular frame 862, such as, for example, up to and adjacent the latch aperture 874. In other embodiments, such as that illustrated in FIG. 16, the guard 872 can be sized so as to not extend to an end surface of the tubular frame 862 but instead extends only to the cutout 871 of the retention wings 870. Similar to other embodiments of the plunger body, such as plunger body 160, the guard 872 can be configured to fit within slots and rails of the metering dial. In other embodiments, other forms of metering devices can be used and the guards 872 can be configured to correspond to similar structural features on such devices.

The guard 872, when positioned between the rails 840, can prevent or substantially reduce the likelihood that the plunger body 860 will rotate after activation. This advantageously can prevent or reduce the likelihood of the plunger body 860 rotating during phases of operation which may cause an erroneous concentration of fluid in the injectable volume. The guard 872 can be sized such that, when the plunger body 860 is fully inserted within the channel 834, the guard 872 can be slightly below the rails 840 such that the plunger body 860 can rotate freely to select different concentration values while in a first, "initial," or "pre-activation" position. However, because the guard 872 is only slightly below the rails 840, once extended a short distance, the guard 872 can become positioned between the selected rails 840. This positioning advantageously allows the guard 872 to lock shortly after activation of the apparatus. Furthermore, the guard 872 can extend outwardly from the tubular frame 860 only a sufficient distance to contact the rails 840 but not sufficiently outwardly to contact variable stops or similar features located between the rails 840.

With continued reference to FIG. 16, the tubular frame 862 can include a latch aperture 874 configured to allow a latch 928 located on the activation rod 920 and contained within the channel 868 to protrude outwardly from the tubular frame 862. As shown in the illustrated embodiment, the latch aperture 874 can be centered just above the topmost portion of the guard 872. In other embodiments, the latch aperture 874 can also be located at different positions along the tubular frame 862 and can contain more than one latch aperture if multiple latches are used.

As described in greater detail below, in a first, "initial", or "pre-activation" position, the latch 928 can be sized so as to not extend beyond the guard 872 and thus not contact a variable stop or similar structure. When in a second or "open" position, the latch 928 can extend outwardly from the tubular frame 862 beyond the guard 872 such that the latch 928 can contact the variable stops or similar structures thereby preventing or significantly reducing the likelihood of further extension of the plunger body 860 while the latch is in the second position. As with other embodiments of the plunger body 860, in some embodiments the latch aperture 874 can be placed such that, if the plunger body 860 is improperly oriented within the metering dial 820 during an initial or "pre-activation" phase of operation, the latch 928 can be prevented from extending outwardly into the second or "open" position by a rail 840 of the metering dial 820. Furthermore, similar to other embodiments of latch mechanisms, this can also prevent or at least substantially reduce the likelihood that a user will be able to operate the activation switch 960 thereby preventing or substantially reducing the likelihood that a user will activate the apparatus when in an inoperable position.

Selector member 866 can be a protrusion extending from the outer surface of the tubular frame 862. The selector member 866 can additionally include a selector indicator 876 which can take the form of a minor protrusion located on the selector ring 866. Selector indicator 876 can correspond to the metering indicators 836 located on the metering body 822 to indicate the concentration level that will be obtained when the plunger body 860 is oriented in that position when activated.

With continued reference to FIG. 16, the handle 864 can extend in two opposite directions in a radial direction from the longitudinal axis of the tubular frame 862. The handle 864 can be shaped such that a user can grip the handle 864 and use the handle to either further extend the plunger body 860 rearwardly, for example, to increase the volume contained in the apparatus or further depress the plunger body 860 frontwardly, for example, to reduce the volume contained in the apparatus and eject the injectable volume. The handle 864 can additionally include a pin aperture 878 for receiving a coupling mechanism, such as a coupling pin, for an activation switch 960. The activation switch 960 can thereby rotate about the coupling mechanism in order to operate an actuation rod 920 which can be located within the plunger body 860.

As will be described in more detail with respect to the operation of an interlock mechanism shown in FIGS. 18-20, the handle 864 can additionally include a recess 880 configured to receive the activation switch 960. The recess 880 can be sized such that, when the activation switch 960 is in a third or "closed" position, the activation switch 960 is fully contained within the recess 880. Furthermore, the handle 864 can additionally include an interlock aperture 882 and an interlock channel 884 configured to receive an interlock member 970 of an interlock mechanism.

Figure 17:
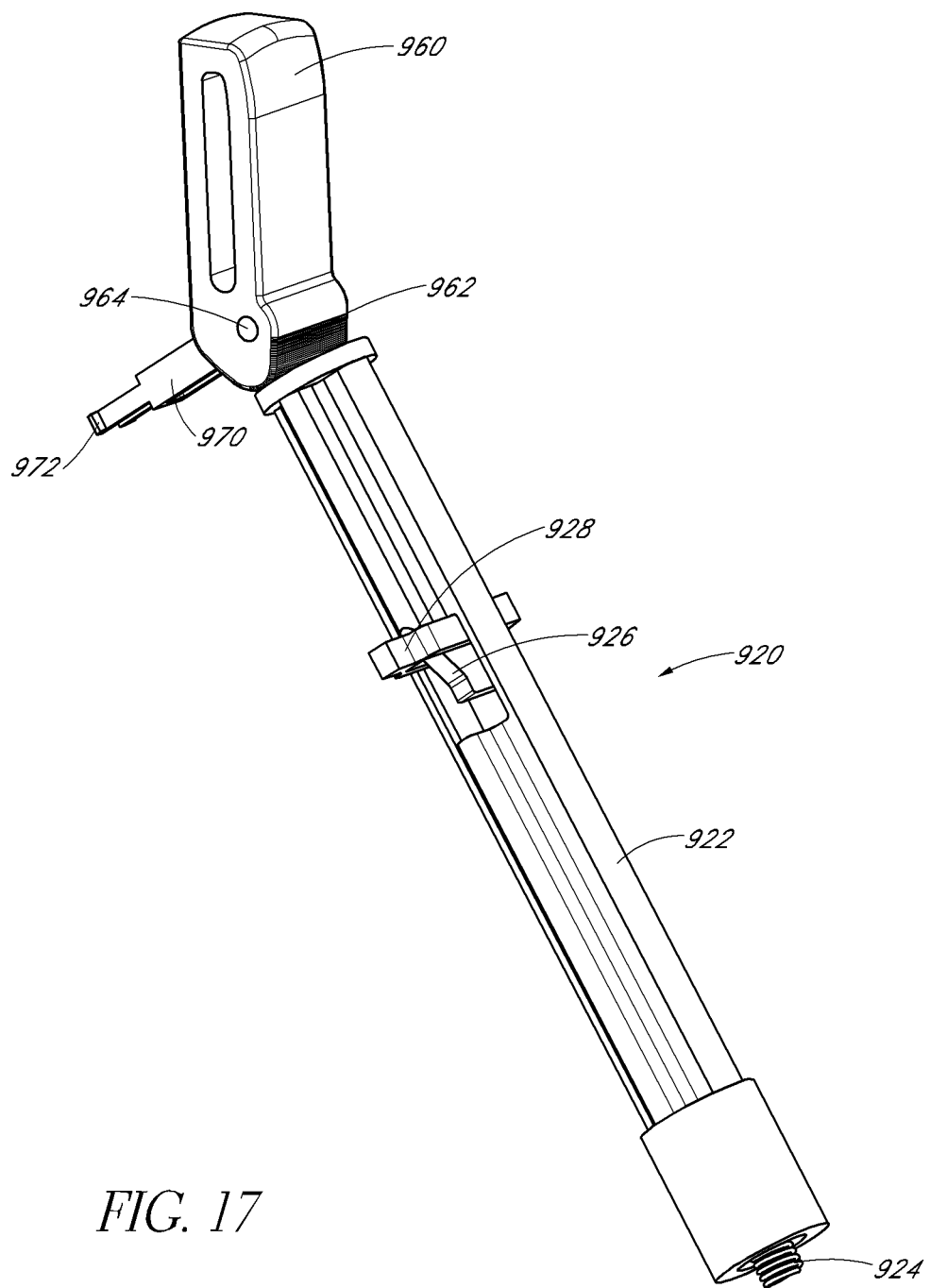
FIG. 17 is a perspective view of components of an embodiment of an activation system.

With reference to FIG. 17, an embodiment of an activation system is shown which can include an actuation rod 920 and an activation switch 960 which can be used to control the operation of the apparatus. As shown in the illustrated embodiment, the actuation rod 920 can include an actuator body 922 with a generally cylindrical shape. The actuator body 922 can be configured to extend through part of the channel 868 of the plunger body 860. In other embodiments, the actuator body 922 can be lengthened or shortened depending on the length of other components contained within the channel 868. In some embodiments, the actuator body 922 can have other cross-sectional shapes such as circles, ovals, ellipses, quadrilaterals, or other polygons. Additionally, the actuator body 922 can differ in cross-sectional shape along different portions of the actuator body 922. For example, as shown in the illustrated embodiment, the actuator body 922 can have a circular cross-sectional shape along a first portion of the actuator body 922 and a "+" cross-sectional shape in a second portion. Similar to other embodiments of the actuation rod, the actuator body 922 can be configured to abut and follow a contoured surface 962 of the activation switch 960 at a first end of the actuator body 922. In some embodiments, the actuator body 922 can be translated within the channel 868 of the plunger body 860 when the activation switch 960 is rotated as a result of the contoured surface 962.

In some embodiments, such as that illustrated in FIG. 17, the actuation rod 920 can include a rod biasing member or mechanism 924 such as a helical spring or any other similar mechanism. The rod biasing member 924 can be configured such that it applies a linearly increasing force as the rod biasing member 924 is compressed. In other embodiments, the rod biasing member 924 can be configured such that it applies an exponentially increasing force as the rod biasing member 924 is compressed such that the force becomes significantly greater as the rod biasing member 924 is compressed. As shown in the illustrated embodiment, the rod biasing member 924 can be a helical spring received in a recess of the actuator body 922. The rod biasing member 924 can be releasably fastened to the actuator body 922 such that the rod biasing member 924 can be removed for purposes of disassembly. In other embodiments, the rod biasing member 924 can be permanently fastened to the actuator body 922. In yet other embodiments, the rod biasing member 924 can be not connected to the actuator body 922 and can be retained within the recess as a result of being placed between two components such as the actuator body 922 and a first housing member 1020.

As is described in further detail below with respect to the operation of an embodiment of the activation system shown in FIGS. 25-27, the rod biasing member 924 can be configured to provide a biasing force against a housing member 1020. This biasing force can be configured such that it can exceed a threshold force to activate the release of gas from a pressurized chamber within the apparatus. In addition, the rod biasing member 924 can also be configured to provide a biasing force against the actuator body 922 such that, when the activation switch 960 is moved into different positions, the actuator body 922 will translate in a direction that will keep the actuator body 922 in contact with at least a portion of the activation switch 960 such as the contoured portion 962.

The actuation rod 920 can include a latch movement portion 926 located between a first end and second end of the actuator body 922. Similar to the latch movement portion of other embodiments of the actuation rods, latch movement portion 926 can be used to translate a latch 928 located thereon such that the latch 928 can protrude from or retract from an aperture or similar structure located on the plunger (e.g., latch aperture 874 located on the plunger body 860).

With continued reference to FIG. 17, an activator switch 960 can be configured to translate the actuator rod 920 through the plunger body 860 towards the first housing member 1020 to activate a mechanism for releasing the gas contained therein. As such, the activator switch 960, like the activator switch of other embodiments, can be a cam with a contoured profile 962 located along the surface configured to contact the actuator body 922. Activator switch 960 can additionally include an aperture 964 configured to receive a pin (not shown in FIG. 17) such that the activator switch 960 can rotate about the pin. It should be appreciated by a person of skill in the art that the activation switch 960 can preferably be any type of switch that can remain in a first, second, or more positions without the user needing to maintain the switch in that position. In the illustrated embodiment, a rotating lever is used. Other switches can also be used such as a screw, latch, spring loaded pin, or any other switch known in the art.

Figure 18:
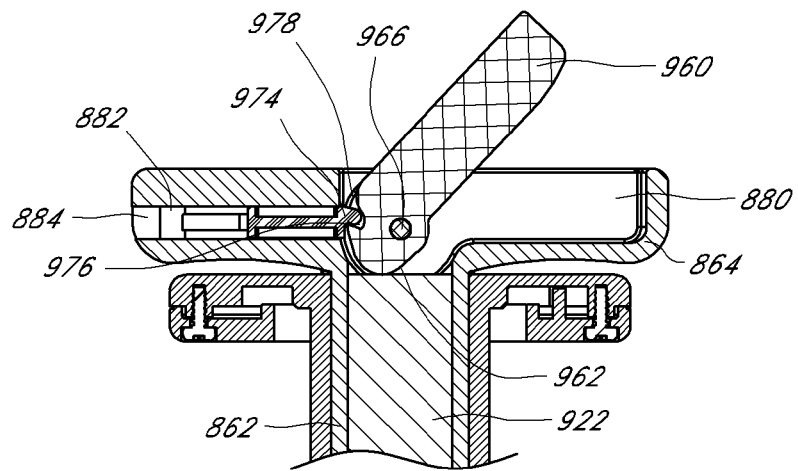
FIG. 18 is a sectional view of a measurement control system and activation system in a first, "initial", or "pre-activation" position showing operation of an interlock mechanism.

With reference to FIG. 18, the activator switch 960 is shown in a first, "initial", or "pre-activation" position. For example, this can be a position prior to a first phase of operation. In this first position, the distance between the pin 966 and the contoured surface 962 in contact with the actuator body 922 can be a first distance such that the actuator body 922 is located at a first distance from the end of the tubular frame 862 of the plunger body 860.

Figure 19:
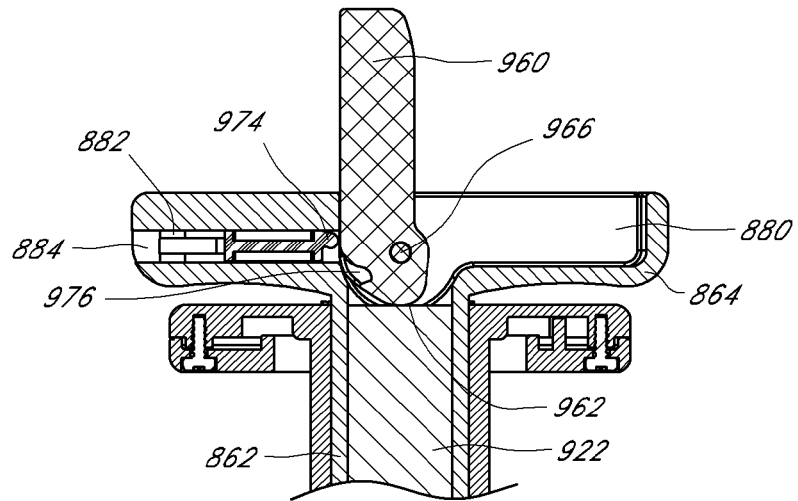
FIG. 19 is a sectional view of a measurement control system and activation system in a second or "open" position showing operation of an interlock mechanism.

As shown in FIG. 19, in some embodiments, the activator switch 960 can be rotated towards a more vertically oriented position, a second or "open" position, in which the distance from the pin 966 to the contoured surface 962 in contact with the actuator body 922 can be a second distance such that the actuator body 922 is located at a second distance from the end of the tubular frame 862 of the plunger body 860. This can correspond to the position of the activation switch 960 during a first and second phase of operation. In some embodiments, the second distance can be greater than the first distance. As will be described in more detail with respect to FIGS. 25-27, this can cause the actuator body 922 to translate towards the first housing member 1020 of the pressurized chamber. This translation can activate the release of fluid or gas contained in the pressurized chamber.

Figure 20:
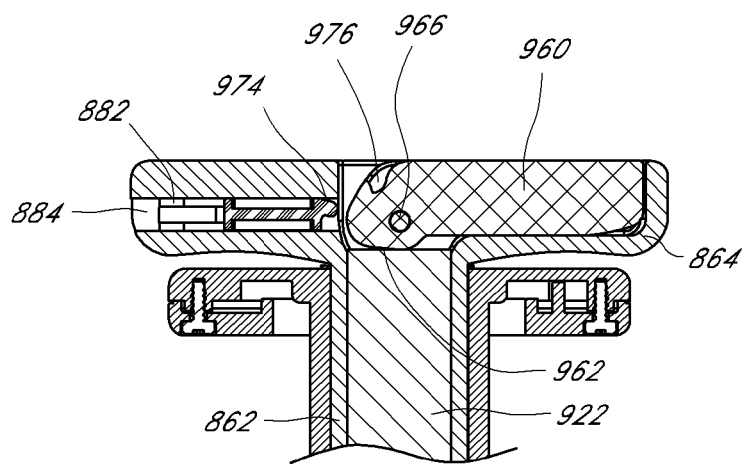
FIG. 20 is a sectional view of a measurement control system and activation system in a third or "closed" position showing operation of an interlock mechanism.

As shown in FIG. 20, in some embodiments, the activation switch 960 can also be rotated towards a more horizontally-oriented position, a third or "closed" position, in which the distance from the pin 966 to the contoured surface 962 in contact with the actuator body 922 can be a third distance such that the actuator body 922 is located at a third distance from the end of the tubular frame 862 of the plunger body 860. This can correspond to a third phase of operation and/or a final phase prior to injection of the injectable volume into a patient. This third distance can be less than or equal to the first and/or second distances. In some embodiments, rotation towards the third position can cause the actuator body 922 to translate away from the first housing member 1020 of the pressurized chamber such that no fluid or gas is released from the pressurized chamber.

With reference back to FIG. 17, an interlock mechanism can be included to control and limit the movement of the activation switch 960. As shown in the illustrated embodiment, the interlock mechanism can include an interlock member 970 such as a pawl having interlock wings or clips 972 located at one end and an interlock portion 974 (shown in FIGS. 18-20) located at a second end. The interlock clips 972 can be configured to be received within interlock apertures 882 or indentations, recesses, or other similar mechanisms to retain the interlock clips 972 located in the handle 864.

With reference again to FIGS. 18-20, an illustration of the operation of an embodiment of the interlock mechanism is provided. FIG. 18 is an illustration of the interlock mechanism and activation switch 960 in the first, "initial", or "pre-activation" position. As shown in the illustrated embodiment, the interlock member 970 can be sized and shaped to be received within an interlock channel 884 of the handle 864. While in the first position, the interlock clips 972 can be biased inwardly by virtue of contact between the interlock clips 972 and the inner surfaces of the channel 884.

As shown in the illustrated embodiment, the interlock portion 974 of the interlock member 970 can be received within a notch or indentation 976 located at an end of the activation switch 960. The shape of interlock portion 974 and the notch or indentation 976 can be chosen such that, while in the first or "initial" position, the activator switch 960 can be prevented or restricted from rotating in a clockwise direction towards a horizontally-oriented position (i.e., the third or "closed" position) due to resulting interference between the interlock portion 974 and the activation switch notch 976. Additionally, the shape of the interlock portion 974 can be chosen such that, in the first position, the activation switch 960 can rotate in a counter-clockwise direction towards a more vertically-oriented position (i.e., the second or "open" position). In some embodiments, such as that shown in the illustrated embodiment, the activation switch 960 can include a second contoured surface 978 configured to translate the interlock member 970 towards an opposite end of the handle 864 when the activation switch 960 is rotated from the first to the second position. In some embodiments, movement of the interlock member 970 within the interlock channel 884 towards an opposite end of the handle 864 results in the ends of the interlock clips 972 being translated towards the interlock apertures 882. Upon reaching the interlock apertures 882, the interlock clips 972 which were originally pre-biased inwardly while in the interlock channel 884, expand outwardly such that the interlock clips 972 are received within the interlock apertures 882. In some embodiments, the interlock member 970 can be prevented from translating back towards the activation switch 960 once received within the interlock apertures 882. This can advantageously prevent or at least substantially reduce the likelihood that the interlock member 970 can reengage the activation switch 960 and restrict movement of the activation switch 960.

FIG. 19 is an illustration of the activation switch 960 and the interlock mechanism in a second or "open" position. As illustrated, the interlock clips 972 of the interlock member 970 have been received within the interlock apertures 882 such that the interlock member 970 can no longer translate back towards the activation switch 960. As a result, a user of the device can rotate the activation switch 960 in a clockwise direction towards the third or "closed" position.

FIG. 20 is an illustration of the activation switch 960 and the interlock mechanism in the third or "closed" position. In some embodiments, the activation switch 960 can be received within a recess 880 in the handle 864 and be flush with a top surface of the handle. Furthermore, the recess 880 can be sized and shaped to closely conform to the shape of the activation switch 960 such that a user of the device can have difficulty rotating the activation switch 960 into one of the prior two positions after the activation switch has been fully placed in the third position.

As such, the interlock mechanism advantageously controls the operation of the activation switch 960 such that a user of the device will not accidentally rotate the switch 960 in an improper position or in an improper order. Furthermore, because a user of the device may have more difficulty rotating the activation switch 960 from the third position to one of the prior two positions, there is a reduced likelihood that a user could potentially alter the concentration of the injectable volume after the final phase of operation. As such, the interlock mechanism advantageously serves as a safety mechanism for operation of the device. In other embodiments, other forms of interlock mechanisms may be used which may include the use of other fasteners, clips, or similar devices. A person of ordinary skill in the art would understand that other types of interlock mechanisms can also be used.

Figure 21:
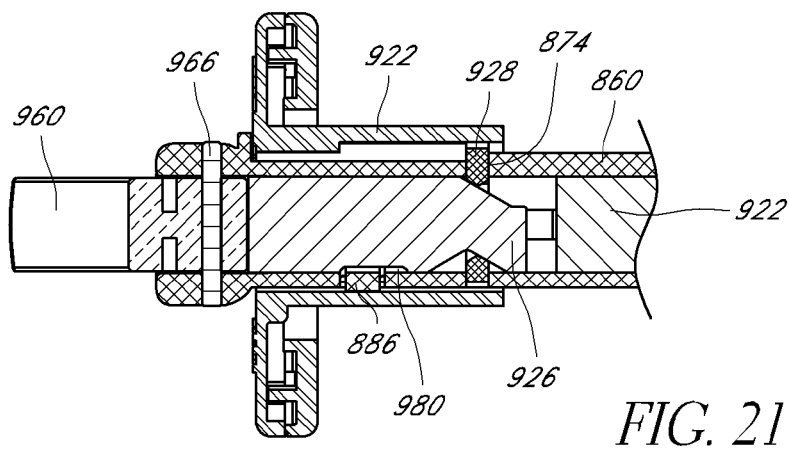
FIG. 21 is a sectional view of a measurement control system and activation system in a first, "initial", or "pre-activation" position showing operation of the latch.
Figure 22:
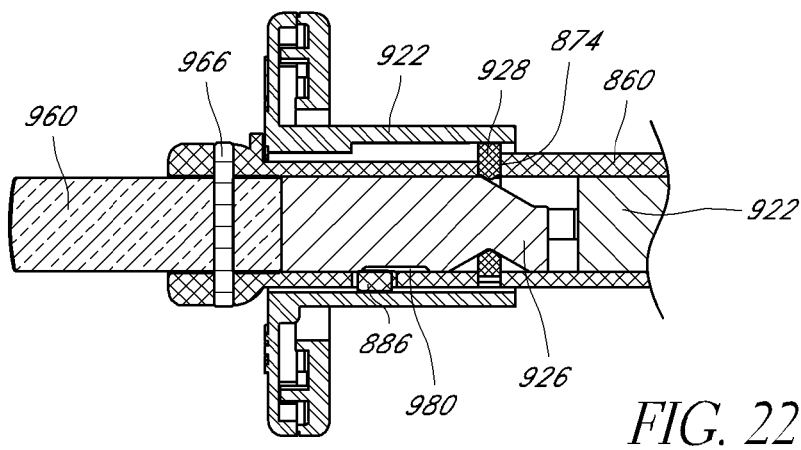
FIG. 22 is a sectional view of a measurement control system and activation system in a second or "open" position showing operation of the latch.
Figure 23:
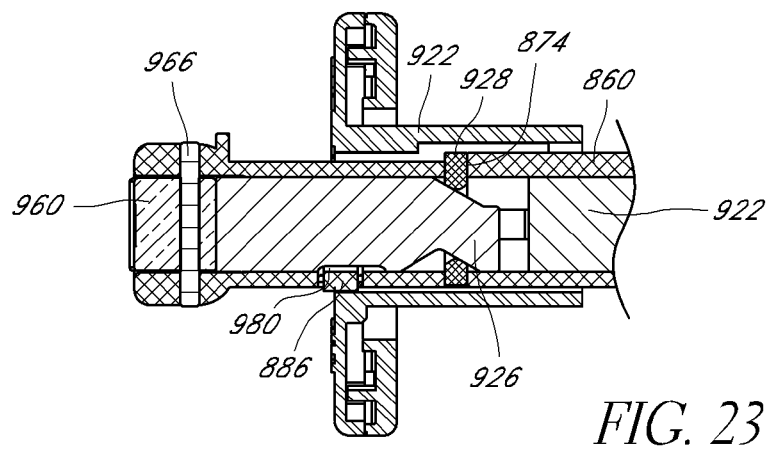
FIG. 23 is a sectional view of a measurement control system and activation system in a third or "closed" position showing operation of the latch.

With reference to FIGS. 21-23, an illustration of the operation of an embodiment of the activation system is shown. As shown in the illustrated embodiment, and similar to other embodiments, the latch 928 can be contained within the latch aperture 874 such that the latch can not translate toward a front end or rear end of the plunger body 860. In such an embodiment, when the actuator rod 920 translates in a frontward or rearward direction, the latch 928 is configured to follow the profile of the latch movement portion 926 of the actuator rod 920.

FIG. 21 shows the embodiment in a first, "initial", or "pre-activation" position. As shown here, the latch 928 can be positioned such that it outwardly protrudes from the plunger body 860 sufficiently such that, if extended rearwardly, the latch 928 would contact a variable stop located on the metering body 922 and prevent any further extension. In other embodiments, when in the first position, the latch 928 can be configured so as to not outwardly protrude from the body 860 to prevent such extension. When moved to the second or "open" position, as shown in FIG. 22, the latch 928 can sufficiently outwardly protrude from the plunger body 860 such that the latch 928 can contact the variable stop or similar structure located on the metering dial 820 thereby preventing any further rearward extension. When rotated to the third or "closed" position, as illustrated in FIG. 23, the latch 928 can be sufficiently retracted within the latch aperture 874 such that the latch 928 no longer contacts the variable stop or similar structure located on the metering dial 820 thereby allowing the plunger body 860 to be further extended rearwardly.

With continued reference to FIGS. 21-23, a ratcheting member 886 such as a pawl can be attached to the plunger body 860. The ratcheting member 886 can be hinged and configured such that the ratcheting member 886 is movably deformable and provides resistance during deformation. The ratcheting member 886 can correspond to features located on the plunger body metering dial 820, such as notches 842, to facilitate proper orientation with respect to the selected concentration. In order to allow inward deformation of the ratcheting member 886, the actuator body 924 can include a recess or indentation 980. This recess 980 can be configured such that the ratcheting member 886 is allowed to inwardly deform only in the first and third positions whereas the ratcheting member 886 is restricted from deforming inwardly while in the second position. This can provide a means of reducing the likelihood that the plunger body 860 can be rotated during operation of the device.

Embodiment of Pressurized Chamber

Figure 24:
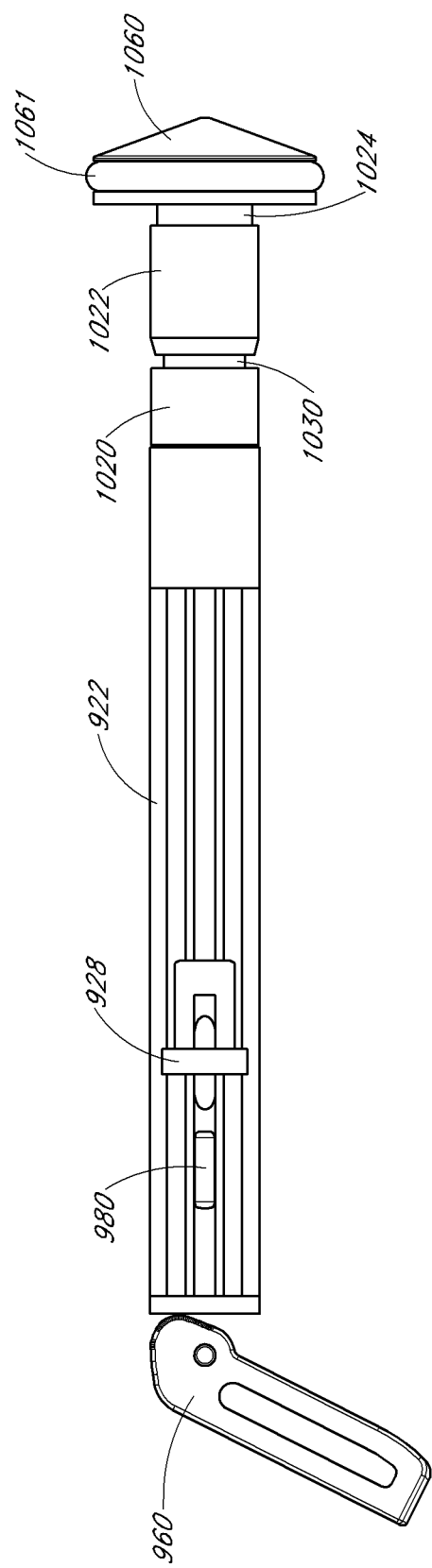
FIG. 24 is an enlarged view of an embodiment of an activation system, pressurized chamber, and a storage member pressure regulation system.

With reference to FIG. 24, an embodiment of a pressurized chamber is shown along with components of an activation system. As illustrated, the pressurized chamber can have a two-part housing with a first housing member 1020 and a second housing member 1022 which are translatable with respect to each other. As shown in the illustrated embodiment, the two members 1020, 1022 can have a generally cylindrical shape such that some or all portions of the two members 1020, 1022 can be received within a channel 868 of the plunger body 860. In some embodiments, the two members 1020, 1022 can be detached from one another to allow free translation of the two members 1020, 1022. In other embodiments, the two-part housing can be attached while still allowing translation of the members 1020, 1022 with respect to each other. Such attachment can be used to increase the stability of the two members 1020, 1022.

As shown in the illustrated embodiment and similar to other embodiments of the pressurized chamber, an annular slot 1024 can be located on the second housing member 1022. In the illustrated embodiment, the annular slot 1024 is located at an end opposite the first housing member 1020 however other possible locations can be chosen. The annular slot 1024 can be sized and configured to receive the retention wings 870 of the plunger body 860 allowing the second housing member 1022 to be fastened to the plunger body 860 using a snap-fit connection. To facilitate insertion of the second housing member 1022 into the channel 868 of the plunger body 860, the inserted end portion can be slightly tapered. In some embodiments, the second housing member 1022 can be removably attached to the plunger body 860 thereby allowing replacement of certain parts contained therein. For example, in some embodiments, a storage member 1030 or canister can be contained within the two-part housing. The two-part housing can also have a plunger end 1060 with a plunger seal 1061 such as a rubber o-ring configured to sealingly contact the syringe body 1120 and form a seal for defining a chamber to contain an injectable volume, such chamber potentially serving as a mixing chamber. Other types of sealing members can be used around the plunger end 1060 to form such a seal.

Figure 25A:
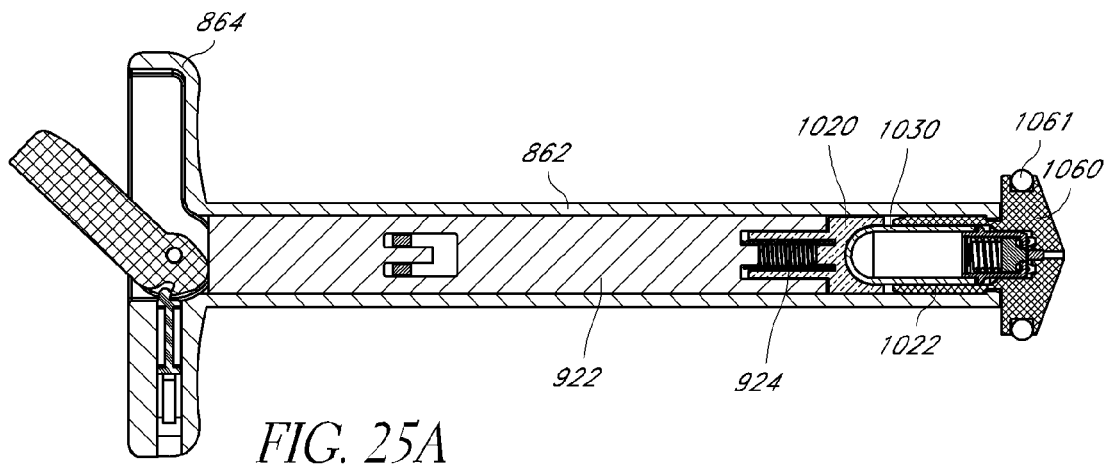
FIG. 25A is a sectional view of the embodiment of an activation system, pressurized chamber, and a storage member pressure regulation system of FIG. 24 in a first, "initial", or "pre-activation" position.
Figure 25B:
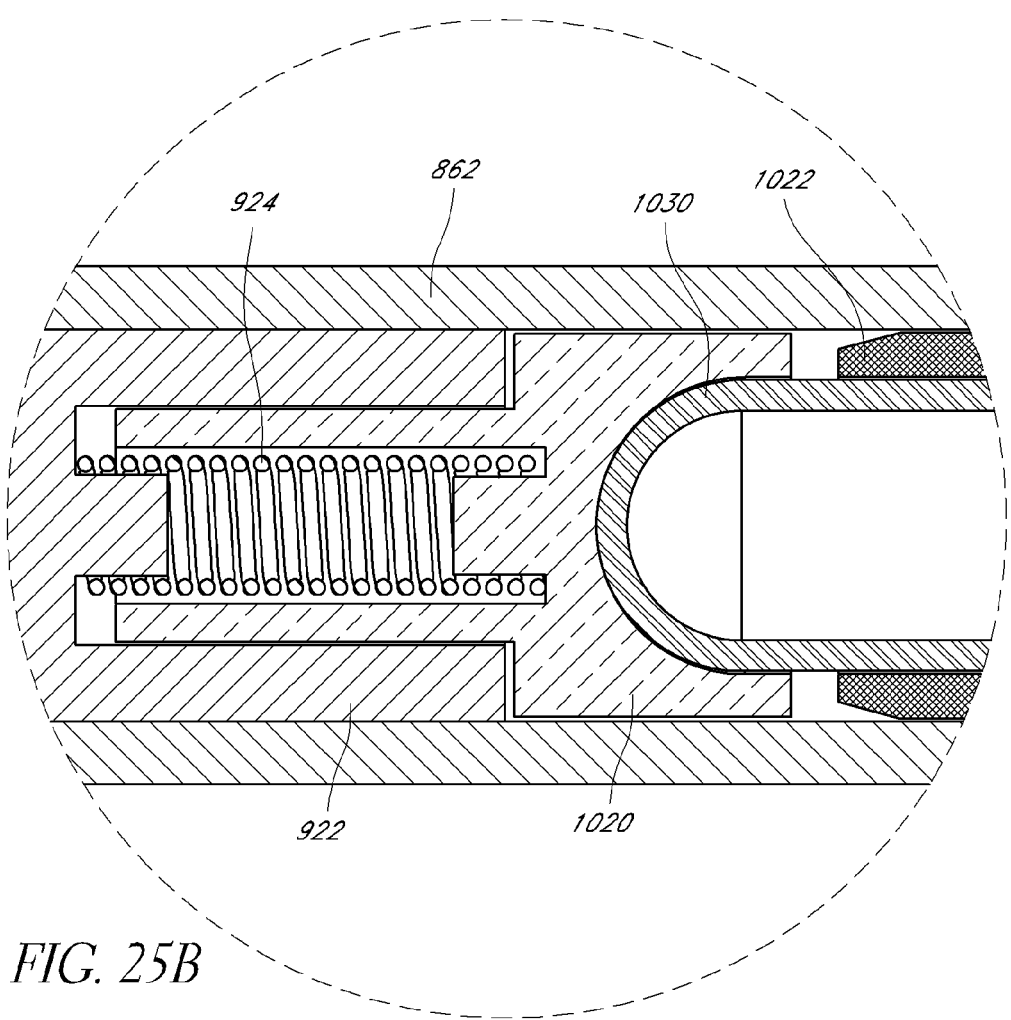
FIG. 25B is an enlarged view of the embodiment of an activation system, pressurized chamber, and a storage member pressure regulation system of FIG. 25A.

FIGS. 25A and 25B are cross-sectional views of the embodiment shown in FIG. 24 when the apparatus is in a first, "initial", or "pre-activation" position. As illustrated more clearly in FIG. 25B, in the first position, the rod biasing member 924, such as a helical spring can be in contact with both the actuator body 922 and the first housing member 1020; however, the actuator body 922 may not be in direct contact with the first housing member 1020. In the first position, the rod biasing member 924 can exert a force in a frontward direction upon the first housing member 1020 and a force in a rearward direction upon the actuator body 922 such that the actuator body 922 remains in contact with the activation switch 960. In this position, the frontward force upon the first housing member 1020 can cause the first housing member 1020 to apply a force upon a storage member 1030 contained therein as the first housing member 1020 attempts to translate towards the second housing member 1022. Preferably, in the first position, the force applied by the first housing member 1020 upon the storage member 1030 will be insufficient to translate the storage member 1030 towards the second housing member 1022 due to mechanisms contained in the storage member 1030 (as will be discussed in further detail in FIGS. 28-29). As such, while in the first position, any gas or fluid contained within the storage member 1030 will remain contained within the storage member 1030.

Figure 26A:
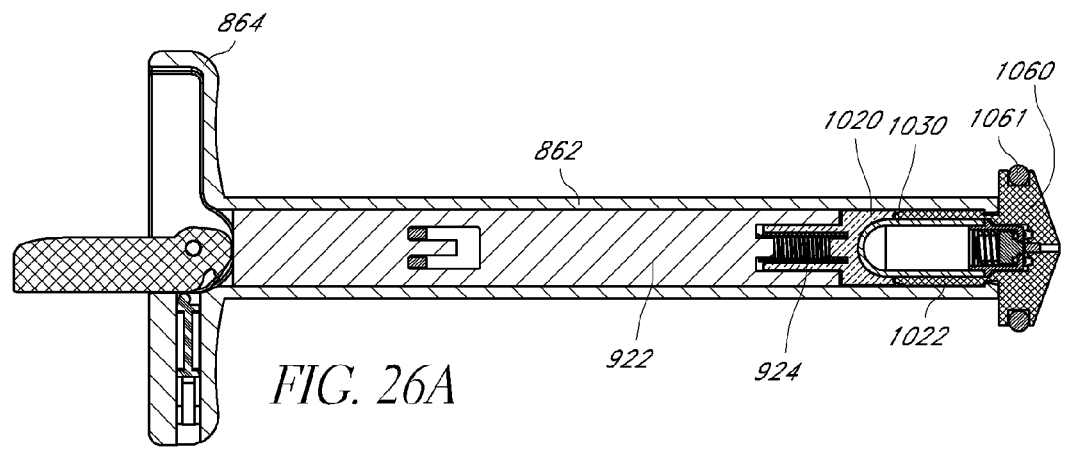
FIG. 26A is a sectional view of the embodiment of an activation system, pressurized chamber, and a storage member pressure regulation system of FIG. 24 in a second or "open" position.
Figure 26B:
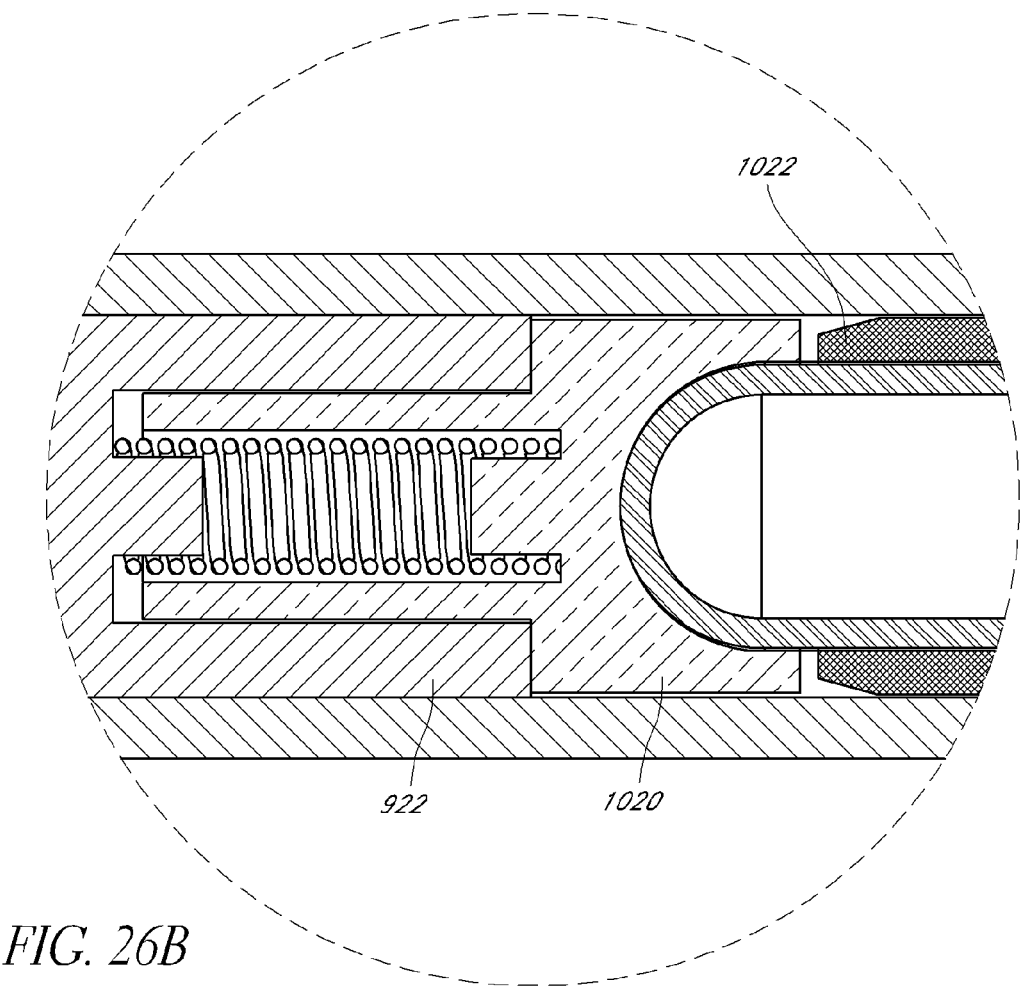
FIG. 26B is an enlarged view of the embodiment of an activation system, pressurized chamber, and a storage member pressure regulation system of FIG. 26A.

FIGS. 26A and 26B are cross-sectional views of the embodiment shown in FIG. 24 when the apparatus is in a second or "open" position. As illustrated more clearly in FIG. 26B, while in the second position, both the actuator body 922 and the rod biasing member 924 can be directly in contact with the first housing member 1020. Due to this direct contact, a more significant force can be applied to the first housing member 1020 such that the first housing member 1020 can translate in a frontward direction thereby causing the storage member 1030 to translate in a frontward direction. This frontward translation of the storage member 1030 can then activate the release of gas from the storage member 1030. In other embodiments, the actuator body 922 need not directly contact the first housing member 1020 since, in such embodiments, the increase in force applied by the rod biasing member 924 due to compression of the rod biasing member 924 can be sufficient to cause the first housing member 1020 to translate in a frontward direction to cause the activation of the release of gas from the storage member 1030.

Figure 27A:
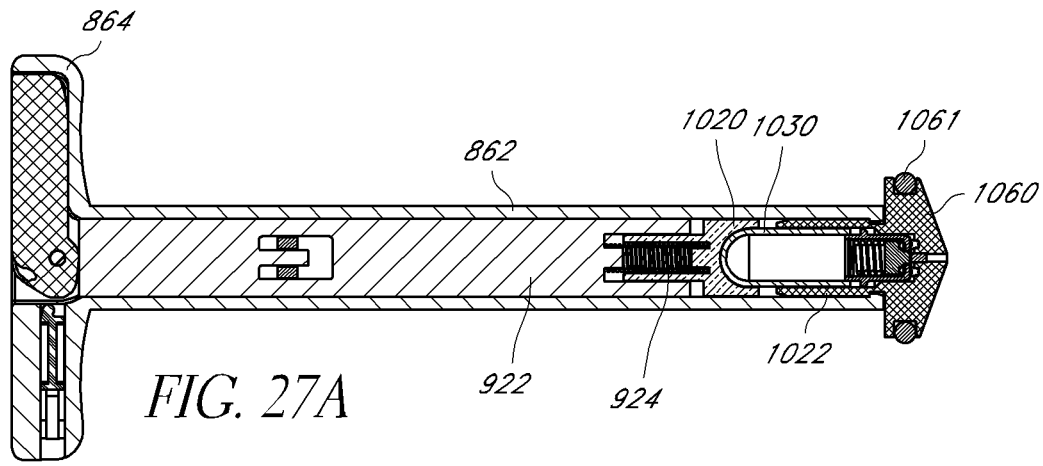
FIG. 27A is a sectional view of the embodiment of an activation system, pressurized chamber, and a storage member pressure regulation system of FIG. 24 in a third or "closed" position.
Figure 27B:
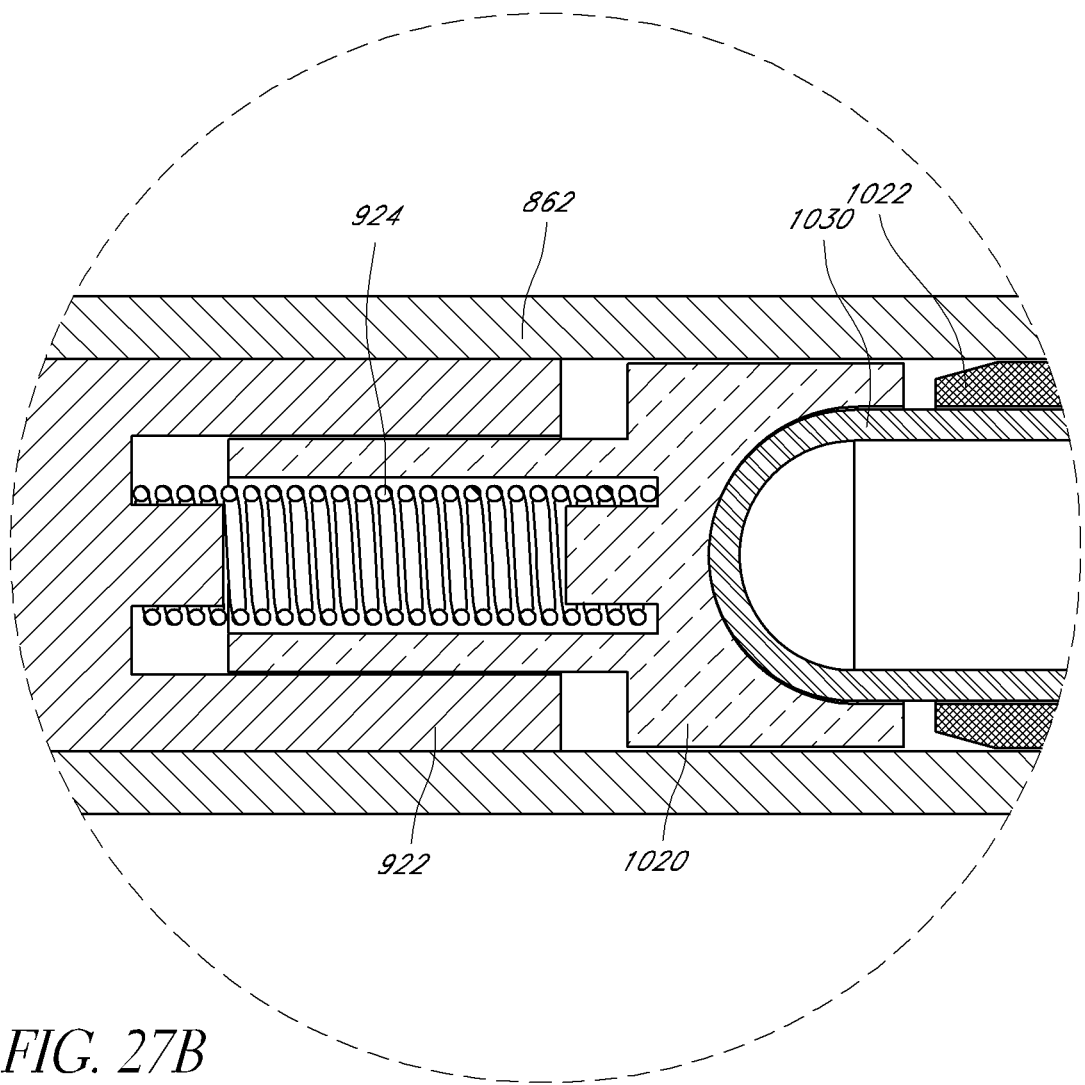
FIG. 27B is an enlarged view of the embodiment of an activation system, pressurized chamber, and a storage member pressure regulation system of FIG. 27A.

FIGS. 27A and 27B are cross-sectional views of the second embodiment shown in FIG. 24 when the apparatus is in a third or "closed" position. As illustrated in FIG. 27B, while in the third position, the actuator body 922 may not be in contact with the first housing member 1020. Furthermore, in some embodiments, due to the reduced distance between the pin 966 and the contoured surface 962, the force exerted by the rod biasing member 924 on the actuator body 922 in a rearward direction can cause the actuator body 922 to translate towards the contoured surface 962 such that the actuator body 922 remains in contact with the activation switch 960. This expansion of the rod biasing member 924 results in a reduction of force exerted by the rod biasing member 924 upon the first housing member 1020. As a result of this reduced force, and as a result of other mechanisms located within the storage member 1030 or canister, the storage member 1030 can be restored to a closed state thereby preventing any additional gas from being released into the chamber to contain the injectable volume, which can also serve as a mixing chamber.

Figure 28:
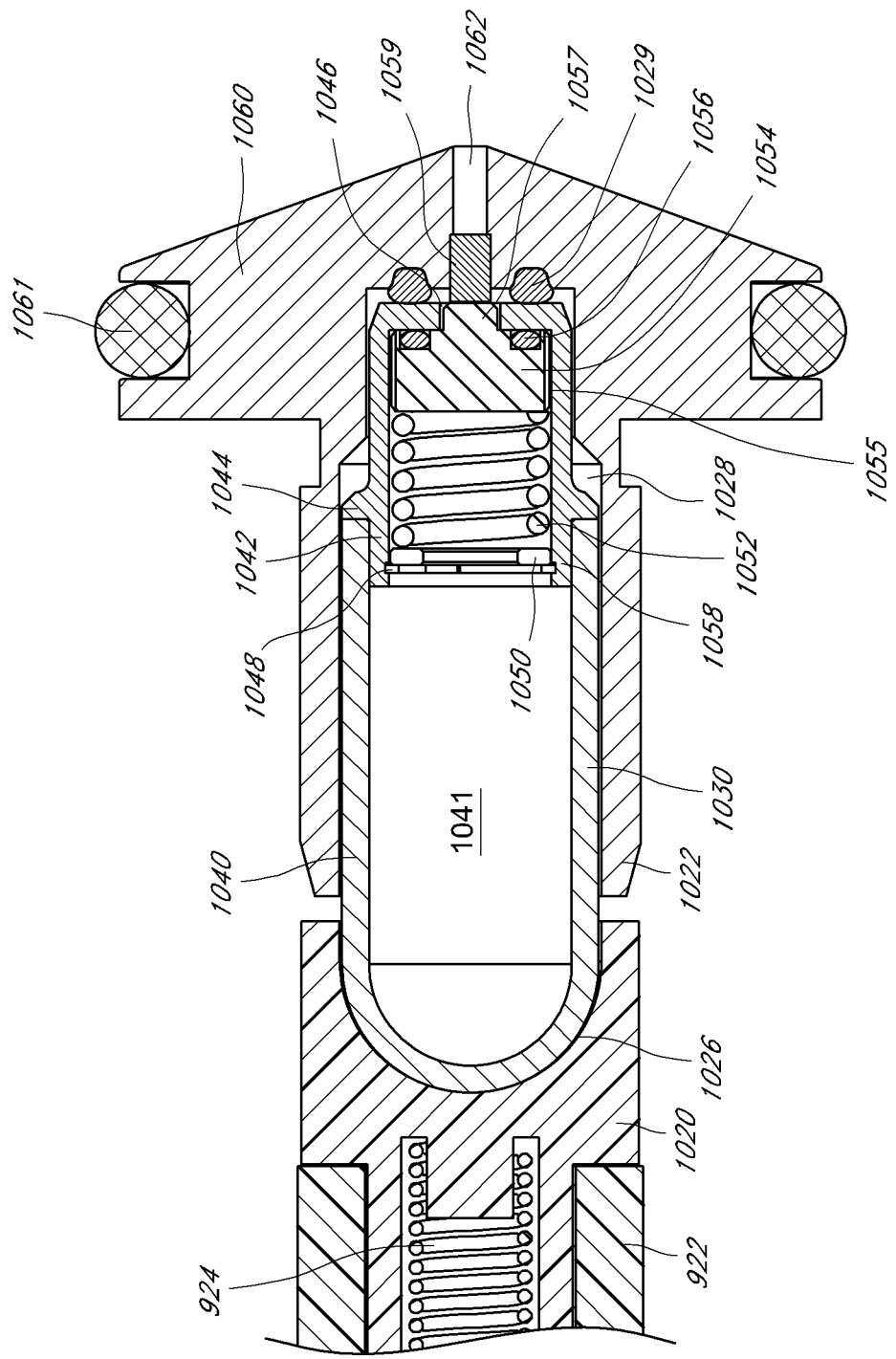
FIG. 28 is an enlarged view of the embodiment of an activation system, pressurized chamber, and a storage member pressure regulation system of FIG. 25A illustrating in more detail an embodiment of a storage member.

FIG. 28 is a sectional view of an embodiment of a pressurized chamber. The first and second housing members 1020, 1022 have contained therein a storage member 1030 or canister, such as a microcylinder, which contains a fluid such as gas. In some embodiments, the second member 1022 has at an end opposite the first member 1020 a conical or frusto-conical surface forming the plunger end 1060. In some embodiments, the second member 1022 and the plunger end 1060 form an integral unit. In other embodiments, the second member 1022 and the plunger end 1060 are separate units which can be attached using a variety of fastening devices and methods such as, but not limited to, fasteners such as screws and pins, retention clips, adhesives, welding, or the like. The plunger end 1060 can have an annular slot 1061 configured to receive a plunger seal 1061 such as a rubber o-ring to form a chamber for the injectable volume, which can also serve as a mixing chamber.

The first housing member 1020 can include a recessed portion 1026 or indented portion configured to contact and receive a first end of the storage member 1030. The shape of the recessed portion 1026 should preferably correspond to the shape of the first end of the storage member 1030. In other embodiments, the first housing member 1020 may not include a recessed portion 1026. The second housing member 1022 can include an interior space 1028 sized and configured to receive a second end of the storage member 1030. In some embodiments, the interior space 1028 can include a housing seal 1029 in contact with the second end of the storage member 1030. In some embodiments, the housing seal 1029 creates a sufficient seal such that little to no gas leaks rearward through the interior space 1028. In some embodiments, the interior space 1028 can also provide a generally snug fit around the storage member 1030 to ensure that the storage member 1030 generally only translates in a frontward and rearward direction. This advantageously reduces the likelihood of the seal between the second end of the storage member 1030 and the housing seal 1029 from being broken.

With continued reference to FIG. 28, the storage member 1030, such as the illustrated canister or microcylinder, can include a body portion 1040 and a head 1042. As shown in the illustrated embodiment, the body portion 1040 can have a generally cylindrical shape with a semi-spherical first end. The body portion 1040, in conjunction with the head 1042, can form an internal volume 1041 to contain a fluid such as a gas in either gaseous or liquid form, or a combination of both, at a first pressure and concentration which can be different than atmospheric gas. For example, such gases can include, but are not limited to, expansile gases, ophthalmic gases such as $SF_6$, $C_3F_8$, $C_2F_6$, or similar gases, propellant gases such as $CO_2$, refrigerant gases such as $N_2O$, and other various types of gases. The size of the interior space 1041 can be chosen such that a unit or single-use dose can be contained within the volume. Other shapes can be chosen for the body portion 1040.

The head 1042 can have a generally tubular shape with an outer diameter matching the inner diameter of the body portion 1040. The head 1042 can have an internal channel and a flange 1044. As shown in the illustrated embodiment, the first end of the head 1042 can have an opening with a diameter that matches the diameter of the channel and the second end of the head can have an opening 1046 with a diameter that is less than the diameter of the channel. In some embodiments, the body portion 1040 and the head 1042 can be separate components which are later attached. This potentially advantageously allows for the assembly of internal components of the head 1042 prior to assembly. Once all components are assembled within the head 1042, the head 1042 can be received within the body portion 1040 and fastened using devices and mechanisms such as adhesives, welding, or the like. In some embodiments, such as that illustrated in FIG. 28, the flange 1044 can abut the body portion 1040 and adhered or welded along this surface. In other embodiments, the body portion 1040 and head 1042 can form an integral unit.

The head 1042 can contain a storage member pressure regulation system, which can form part of a first pressure regulation system, and which can take the form of an internal valve mechanism within the channel. The internal valve mechanism can include a retaining ring 1048, a valve seat 1050, an internal biasing member or mechanism 1052 such as a spring, a valve piston 1054, and a piston seal 1056. The retaining ring 1048 can be placed within an annular slot 1058 located on the head 1042. The retaining ring 1048 can be made of an elastic material such that the retaining ring can be deformed prior to fitting into slot 1058. The valve seat 1050 can be placed between the retaining ring 1048 and the second end of the head 1042. In some embodiments, the valve seat 1050 can be a ring having an outer diameter approximately equal to the internal diameter of the head 1042.

The valve piston 1054 can have a generally cylindrical shape and be placed between the seat 1050 and the second end of the head 1042. The outer diameter of the valve piston 1054 can be chosen to be approximately equal to the internal diameter of the head 1042. As shown in the illustrated embodiment, the valve piston can include an annular slot configured to receive the piston seal 1056, fluid pathways 1055 or channels located along the perimeter of the piston, and a protrusion 1057. The fluid pathways 1055 can be configured to allow fluid to pass between the valve piston 1054 and the head 1042. In the illustrated embodiment, a total of four fluid pathways are included; however, fewer or greater numbers of pathways can be used. In some embodiments, the protrusion 1057 can be a cylindrical member having a smaller diameter that corresponds to the diameter of the opening 1046. The protrusion 1057 can be configured to fit within the opening 1046. In some embodiments, the protrusion 1057 can be flush with the end surface of the head 1042. In other embodiments, the protrusion 1057 can be recessed within the opening or extend beyond the end surface. A biasing mechanism 1052 can be placed between the seat 1050 and the piston 1054 to apply a force on the valve piston 1054 in a frontward direction such that a seal is formed between the piston seal 1056 and the head 1042. In other embodiments, other types of valve designs can be used such as a ball valve, poppet valve, or any other valve mentioned herein or known in the art.

In some embodiments, the internal biasing mechanism 1052 can be configured such that, when an activation switch is in a first or "pre-activation" position, the internal valve mechanism will not open as a result of any forces applied to it such as the force applied to the storage member 1030 via the first housing member 1020 as a result of the rod biasing mechanism 924. In some embodiments, the internal biasing mechanism 1052 can be configured such that, when an activation switch is in a second or "open" position, the internal valve mechanism will open as a result of forces applied to it. In some embodiments, the internal biasing mechanism 1052 can be configured such that, when an activation switch is in a third or "closed" position, the internal valve mechanism will not open as a result of any forces applied to it such as the force applied to the storage member 1030 via the first housing member 1020 as a result of the rod biasing mechanism 924.

In some embodiments, the storage member 1030 can include other structures such as filters integrated in portions of the storage member 1030 such as the head 1042. The storage member 1030 can include membranes or other sealing structures placed over the head 1042 and over the opening 1046 to provide an additional seal which can advantageously extend the shelf life of the storage member 1030. The membrane or sealing structure can be punctured by a protruding member, such as a pin 1059, or any other similar release mechanism. In some embodiments, the release mechanism can be a porous material, for example, known as "frit". The storage member 1030 can also include additional valve members which can serve as a relief valve to reduce the likelihood of rupturing if the pressure contained within the storage member 1030 exceeds certain operational limits. The storage member 1030 can also be configured to rupture in a controlled manner to reduce the likelihood of catastrophic failure.

In some embodiments, the storage member 1030, and the internal components such as the internal valve, is manufactured from materials that are both small and light-weight. The material can also be flexible. In some embodiments, the materials and dimensions of the storage member 1030 can be chosen such that the storage member 1030 resists diffusion of gas through the walls of the storage member 1030. This can provide the advantage of increasing storage life of the storage member 1030 when a gas is contained therein. In some embodiments, the length of the storage member 1030 from a rearward most end of the body 1040 and a frontward most end of the head 1042 can range from approximately 15 mm to approximately 65 mm, from approximately 20 mm to approximately 45 mm, and from approximately 25 mm to approximately 35 mm, such as 29 mm. In some embodiments, the outer diameter of the body 1040 can range from approximately 4 mm to approximately 25 mm, from approximately 6 mm to approximately 20 mm, and from approximately 8 mm to approximately 15 mm, such as 9.5 mm. In some embodiments, the outer diameter of the head 1042, not including a flange portion can range from approximately 2 mm to approximately 20 mm, from approximately 4 mm to approximately 15 mm, and from approximately 6 mm to approximately 10 mm, such as 7.5 mm.

Figure 29:
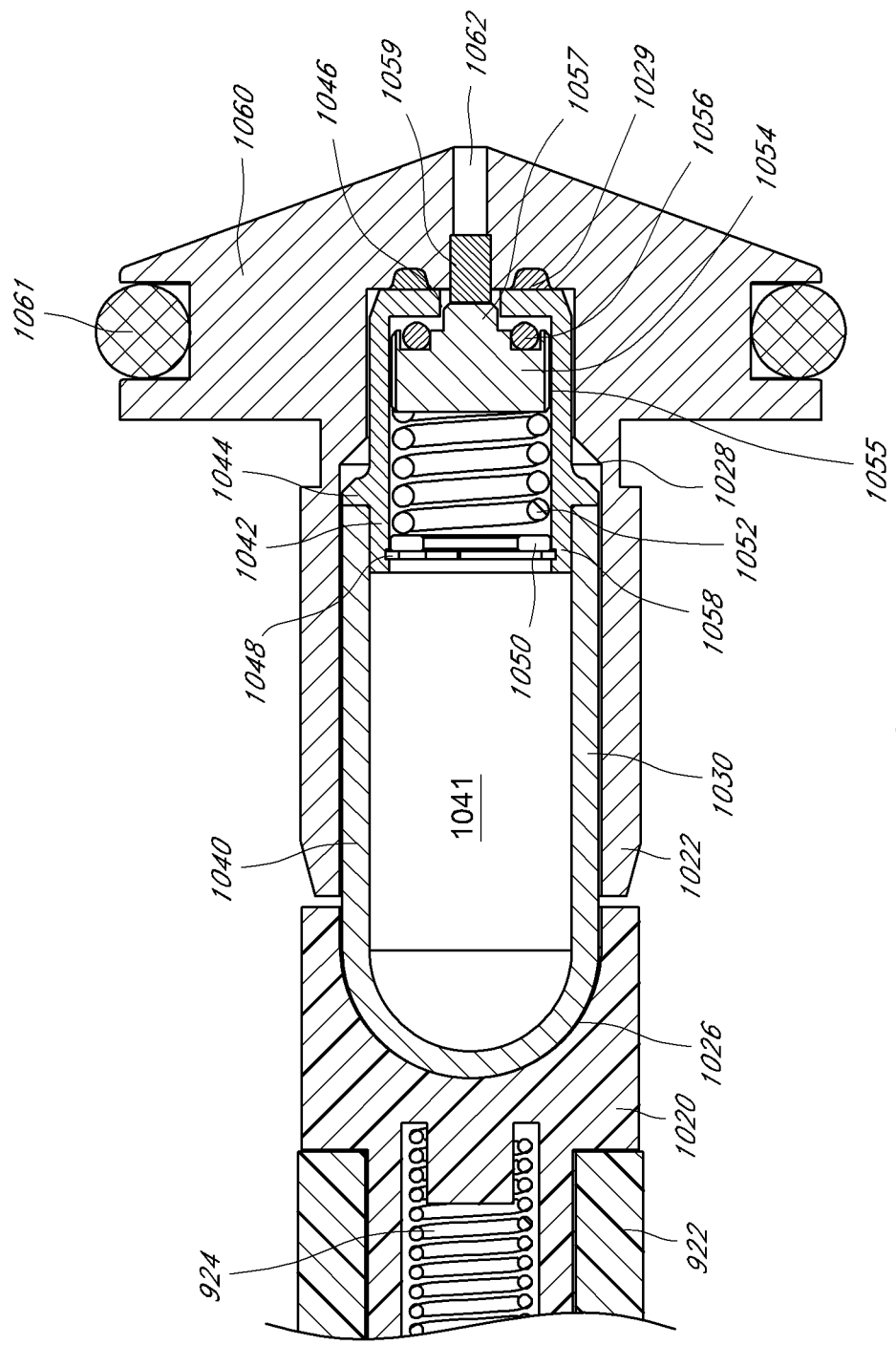
FIG. 29 is an enlarged view of the embodiment of an activation system, pressurized chamber, and a storage member pressure regulation system of FIG. 26A illustrating in more detail an embodiment of a storage member.

With continued reference to FIG. 28, the second housing member 1022 can include a release mechanism 1059 located within a channel 1062. The release mechanism 1059 can be substantially centered over the protrusion 1057 of the valve piston 1054 and have a diameter which matches the diameter of the opening 1046. As illustrated in FIG. 29, during operation, when the storage member 1030 is translated in a frontward direction towards the release mechanism 1059, the release mechanism 1059 remains stationary such that the release mechanism 1059 can cause the valve piston 1056 to unseat from the head 1042 thereby allowing the flow of fluid from the storage member 1030, past the pathways 1055 and the release mechanism 1059, and through the channel 1062 where it ultimately can flow into a chamber for the injectable volume, such as a mixing chamber. In some embodiments, the release mechanism 1059 can be made out of a porous material such that the release mechanism 1059 itself serves as a preliminary filtering mechanism for fluid flowing through channel 1062. In some embodiments, filters can be added between the release mechanism 1059 and the end of the channel 1062 or at any other location to filter out materials.

Figure 30:
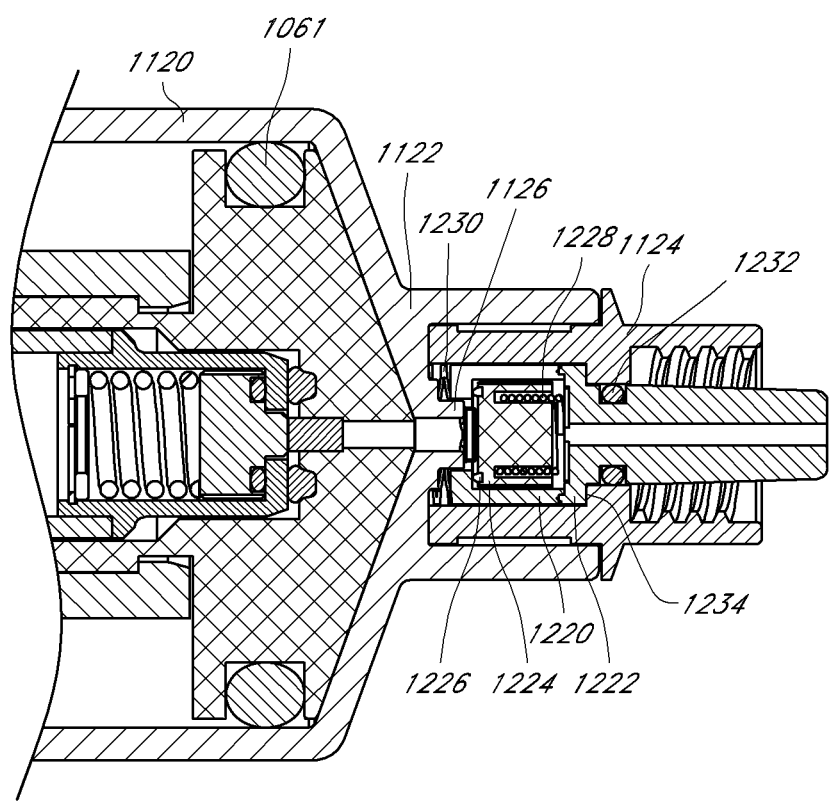
FIG. 30 is a sectional view of an embodiment of a syringe body and syringe pressure regulation system.

With reference to FIG. 30, an embodiment of a chamber for an injectable volume, such as a mixing chamber, is shown which can include a syringe body 1120, a syringe pressure regulation system, which can form part of a second pressure regulation system, and various components of the above-mentioned systems. Syringe body 1120 can have a cylindrical body and a nose 1122 at a front end. In some embodiments, a threaded nozzle 1124, which can include multiple components of a pressure regulation system, can be removably attached to the nose 1122 of the syringe body 1120. This can advantageously facilitate assembly of the apparatus by allowing the pressure regulation system to be assembled within the smaller nozzle 1124 prior to being incorporated with the syringe body 1120. The nozzle 1124 can be attached to the nose 1122 using multiple fastening devices and means such as screws, adhesives, snap fits, welding, or the like. The chamber for an injectable volume can be defined by the inner walls of the syringe body 1120 and the plunger seal 1061. Furthermore, as with other embodiments of the syringe, the syringe body 1120 can also include indicators along its outer surface corresponding to a chosen concentration and a flange at a rear end of the body 1120 configured to be attached to a metering dial.

With continued reference to FIG. 30, an embodiment of the syringe pressure regulation system is shown comprising a valve body 1220, a valve end 1222, a valve piston 1224, a piston seal 1226, a piston biasing member or mechanism 1228, a valve biasing member or mechanism 1230, and a valve end seal 1232. Similar to other embodiments of the pressure regulation system, the valve body 1220 and valve end 1222 can slidingly translate within the threaded nozzle 1124.

In a first position, such as that illustrated in FIG. 30, the valve end 1222 can rest against a lip 1234 of the threaded nozzle 1124 due to force exerted by the valve biasing member 1230 on the valve body 1220 and valve end 1222 in a frontward direction. In the first position, the valve piston 1224 and valve seal 1226 can form a seal and limit, or prevent, the passage of fluid through the valve body 1220. However, when the pressure in the chamber for an injectable volume increases beyond a threshold value to overcome the biasing force exerted by the piston biasing member 1228, the valve piston 1224 can be translated in a frontward direction against the force applied by the piston biasing member 1228 and fluid can pass through the valve body 1220 and valve end 1222 and into the atmosphere. Once the pressure reduces back to a threshold value, the equilibrium of forces allows the valve piston 1224 and valve seal 1226 to once again sealingly contact the valve body 1220.

In a second position, the valve body 1220 and valve end 1222 can be translated in a rearward direction against the valve biasing member 1230. For example, this can be accomplished by applying a force in the rearward direction upon the valve end 1222. In the second position, contact between the valve piston 1224 and an internal protruding member 1126 of the syringe body 1120 can cause the valve piston 1224 to move in a rearward direction relative to the valve body 1220 and valve end 1222 such that the valve piston 1224 no longer sealingly contacts the valve body 1220. This could, in some embodiments, allow the passage of fluid to and from the chamber for an injectable volume. In some embodiments, the pressure regulation system can be forced into a second position when an inline filter is threaded onto the threaded nozzle 1124. For example, an attachment 760 as illustrated in FIG. 14. Other types of attachments, such as stopcocks, valves, tubing, or the like, can also be attached to the threaded nozzle 1124.

External Gas Filling

In some embodiments, the pressurized chamber can be external to the apparatus. In such embodiments, the pressurized chamber can be a tank or other canister containing the gas in liquid or gaseous (or a combination) form. In some embodiments, the tank can be attached to the threaded nozzle via tubing or other mechanisms. The connection between the threaded nozzle and tubing can cause the pressure regulation system located on the apparatus to be forced open thereby allowing the gas from the tank to be input into the chamber. In some embodiments, introduction of the gas from the tank can be performed during a first phase of operation. As such, the gas from the tank can fill the apparatus with gas until the apparatus reaches a configured first volume. In some embodiments, the tank can have a regulator such that the apparatus is filled with gas at a regulated pressure. The connection can then be removed from the threaded nozzle, allowing the valve to function normally. In some embodiments, since the gas can be at a higher pressure than atmospheric air and can exceed a threshold value for the pressure regulation system, the gas can be expelled or bled from the system until a configured pressure is achieved in the apparatus. Once the configured pressure is achieved in the apparatus, the remaining phases of operation can then be completed in a similar manner to those in the above-described embodiments.

The foregoing description is that of an apparatus and method for mixing and/or injecting gases having certain features, aspects, and advantages in accordance with the present inventions. Various changes and modifications also can be made to the above-described gas mixture apparatus and method without departing from the spirit and scope of the inventions. Thus, for example, those skilled in the art will recognize that the invention can be embodied or carried out in a manner that achieves or optimizes one advantage or group of advantages as taught herein without necessarily achieving other objects or advantages as can be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of the specific features and aspects of the embodiments can be made and still fall within the scope of the invention. Accordingly, it should be understood that various features and aspects of the disclosed embodiments can be combined with or substituted for one another in order to form varying modes of the disclosed gas mixture apparatus.

What is claimed is:

1. A hand-held gas mixer and injector assembly, comprising:
   a syringe body with an outlet, the outlet comprising a nozzle and a valve disposed in the nozzle, the valve having a closed configuration and an open configuration;
   a plunger slidably disposed in the syringe body and, with the syringe body, defining a first chamber within the syringe body, the first chamber fluidically connected to the outlet such that fluid can be drawn into the first chamber through the outlet and discharged from the first chamber through the outlet;
   a filter having a first end connectable to the outlet of the syringe body and configured to maintain the valve in the open configuration when connected to the outlet of the syringe body.

2. The hand-held gas mixer and injector assembly of claim 1, wherein the first end of the filter comprises a flange configured to engage a threaded interior section of the nozzle.

3. The hand-held gas mixer and injector assembly of claim 1, wherein the filter comprises a second end comprising a filter orifice and a lumen extending between the first end and the second end, the filter configured to filter fluid flowing between the first end and the second end.

4. The hand-held gas mixer and injector assembly of claim 3, wherein the filter further comprises a filter element positioned between the first end and the second end.

5. The hand-held gas mixer and injector assembly of claim 1, wherein the valve comprises a valve body, a piston, a seal, a valve biasing member, and an internal protruding member.

6. The hand-held gas mixer and injector assembly of claim 5, wherein at least a portion of an inner surface of the filter tapers so as to correspond to a shape of the valve body.

7. The hand-held gas mixer and injector assembly of claim 1, further comprising a filling mechanism configured to direct a first fluid into the first chamber so as to move the plunger and expand the first chamber.

8. The hand-held gas mixer and injector assembly of claim 7, further comprising a second chamber, the second chamber comprising an internal volume containing at least the first fluid in a concentration different than that in atmospheric air and at a pressure greater than that of surrounding atmospheric air.

9. The hand-held gas mixer and injector assembly of claim 8, wherein the valve comprises a first valve, wherein the second chamber comprises an opening at a first end and a second valve located adjacent the first end, the second valve configured to seal the opening.

10. The hand-held gas mixer and injector assembly of claim 9, wherein the second valve comprises a piston, a seal, and a biasing member, the second valve configured to seal the opening at least prior to activation of the assembly.

11. The hand-held gas mixer and injector assembly of claim 8, wherein the second chamber comprises a relief valve configured to release the first fluid from the second chamber when the pressure within the second chamber exceeds a preconfigured value.

12. The hand-held gas mixer and injector assembly of claim 1, further comprising a release mechanism, wherein the release mechanism comprises a pin.

13. The hand-held gas mixer and injector assembly of claim 1, further comprising an adjustable volume limiter configured to limit movement of the plunger to a plurality of user-selectable positions corresponding to a plurality of volumes of the first chamber.

14. The hand-held gas mixer and injector assembly of claim 1, wherein the plunger is slidably disposed within the syringe body and moveable along an axial direction, the outlet comprising an outlet passage extending along the axial direction.

15. A method for mixing gases, comprising:
providing a syringe comprising:
a syringe body with an outlet, the outlet comprising a nozzle and a valve disposed in the nozzle, the valve having a closed configuration and an open configuration; and
a plunger slidably disposed in the syringe body and, with the syringe body, defining a first chamber within the syringe body; and
connecting a first end of a filter to the nozzle and thereby transitioning the valve from the closed configuration to the open configuration.

16. The method of claim 15, wherein the valve comprises a valve body, a piston, a seal, a valve biasing member, and an internal protruding member and wherein connecting the first end of the filter to the nozzle causes the piston to move in a rearward direction relative to the valve body so as to disrupt a sealing contact between the valve piston and valve body.

17. The method of claim 15, wherein connecting the first end of the filter to the nozzle comprises engaging a flange of the filter with a threaded interior section of the nozzle.

18. The method of claim 15, further comprising adjusting a volume selector to a first volume value on an adjustable volume limited syringe, the selected first volume value corresponding to a first volume of a first chamber of the syringe.

19. The method of claim 18, further comprising:
releasing a first fluid into the first chamber of the syringe, the first fluid having a pressure higher than that of surrounding atmospheric air; and
expanding the first chamber to the first volume, wherein the expansion of the first chamber to the first volume occurs as a result of an increase in pressure in the first chamber due to filling of the first chamber with the first fluid.

20. The method of claim 19, wherein releasing the first fluid into the first chamber comprises releasing the first fluid from a second chamber disposed within at least one of the syringe body and the plunger.

* * * * *